United States Patent
Ashkenazi et al.

(10) Patent No.: US 6,558,661 B1
(45) Date of Patent: May 6, 2003

(54) TREATMENT OF INFLAMMATORY BOWEL DISEASE WITH IFN-γ INHIBITORS

(75) Inventors: Avi J. Ashkenazi, San Mateo; Rebecca H. R. Ward, San Francisco, both of CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 08/190,204

(22) PCT Filed: Dec. 9, 1993

(86) PCT No.: PCT/US93/11966

§ 371 (c)(1),
(2), (4) Date: Feb. 22, 1994

(87) PCT Pub. No.: WO94/14467

PCT Pub. Date: Jul. 7, 1994

Related U.S. Application Data

(63) Continuation-in-part of application No. 07/997,835, filed on Dec. 29, 1992, now abandoned.

(51) Int. Cl.⁷ .................. A61K 38/19; A61K 39/395; C07K 14/52; G01N 33/53
(52) U.S. Cl. .................. 424/85.4; 424/85.5; 424/130.1; 424/133.1; 424/143.1; 530/300; 530/350; 530/351; 530/386; 514/2; 435/7.1
(58) Field of Search .................. 424/85.4, 85.5, 424/130.1, 133.1, 143.1; 530/300, 350, 351, 386; 514/2; 435/7.1

(56) References Cited

U.S. PATENT DOCUMENTS

| | | | |
|---|---|---|---|
| 4,676,982 A | 6/1987 | Hässig | 424/85 |
| 4,727,138 A | 2/1988 | Goeddel et al. | 536/27 |
| 4,762,791 A | 8/1988 | Goeddel et al. | 435/243 |
| 4,897,264 A | 1/1990 | Novick et al. | 424/85.5 |
| 4,925,793 A | 5/1990 | Goeddel et al. | 435/69.51 |
| 4,929,554 A | 5/1990 | Goeddel et al. | 435/172.3 |

FOREIGN PATENT DOCUMENTS

| | | |
|---|---|---|
| EP | 240975 | 10/1987 |
| EP | 369413 | 5/1990 |
| EP | 393502 | 10/1990 |
| EP | 416652 | 3/1991 |
| WO | WO 90/14359 | 11/1990 |

OTHER PUBLICATIONS

Auguet et al., "Molecular Cloning and Expression of the Human Inteferon–γ Receptor" *Cell* 55:273–280.

Brandtzaeg, P. et al., "Immunopathology of Crohn's Disease", *Ann. Gastroenterol. Hepatol.* 21(4), 201–220 (1985).

Coffman and Carty, "A T cell activity that enhances polyclonal IgE production and its inhibition by interferon–γ", *J. Immunol.* 136: 949–954 (1986).

Cominelli, F. et al., "Interleukin 1 (IL–1) gene expression, synthesis and effect of specific IL–1 receptor blockade in rabbit immune complex colitis", *J. Clin. Invest.* 86: 972–980 (1990).

Döbeli, H. et al., "Role of the carboxy–terminal sequence on the biological activity of human interferon (IFN–γ)", *J. Biotech.* 7: 199–216 (1988).

Ealick, S.E. et al., "Three–dimensional structure of recombinant human interferon–γ", *Science* 252: 698–702 (1991).

Fais, S. et al., "HLA–DR antigens on colonic epithelial cells in inflammatory bowel disease: I. Relation to the state of activation of lamina propria lymphocytes and to the epithelial expression of other surface markers", *Clin. Exp. Immunol.*, 68: 605–612 (1987).

Favre, C. et al., "Epitope mapping of recombinant human gamma interferon using monoclonal antibodies", *Mol. Immunol.* 26(1):17–25 (1989).

Hochkeppel and de Ley, "Monoclonal antibody against human IFN–γ", *Nature* 296 (5854):258–259 (1982).

Hogrefe, H. H. et al., "Amino terminus is essential to the structural integrity of recombinant human interferon–γ", *J. Biol. Chem.* 264 (21):12179–12186 (1989).

Jarpe, M.A. et al., "Topology of receptor binding domains of mouse IFN–γ", *J. Immunol.* 145:3304–3309 (1990).

Kuhn R. et al., "IL–4 and Il–10 deficient mice", *8th Int'l. Congress of Immunology*, abstract No. 18 Budapest, Hungary, Aug. 22–28, 1992.

Khurana Hershey and Schreiber, "Biosynthetic Analysis of the Human Interferon–γ Receptor", *J. Biol. Chem.* 264(20): 11981–11988 (1989).

Kürschner, C. et al., "Construction Purification and Characterization of New Interferon γ (IFNγ) Inhibitor Proteins", *J. Biol. Chem.* 267(13): 9354–9360 (1992).

Kusugami, K. et al., "Intestinal immune reactivity to interlukin 2 differs among Crohn's disease, ulcerative colitis and controls", *Gastroenterology* 97: 1–9 (1989).

Leinikki, P. O. et al., "Reduced receptor binding by a human interferon–γ fragment lacking 11 carboxyl–terminal amino acids," *J. Immun.* 139(10):3360–3366 (1987).

Ligumsky, M. et al., "Role of interleukin 1 in inflammatory bowel disease–enhanced production during active disease", *Gut* 31: 686–689 (1990).

Lord, S.C. et al., "Functional domains of human interferon gamma probed with antipeptide antibodies", *Mol. Immun.* 26(7):637–640 (1989).

MacDermott, R.P. et al., "Alterations in serum immunoglobulin G sublcasses in patients with ulcerative colitis and Crohn's disease", *Gastroenterology* 96: 764–768 (1989).

(List continued on next page.)

*Primary Examiner*—Yvonne Eyler
*Assistant Examiner*—Nirmal S. Basi
(74) *Attorney, Agent, or Firm*—Merchant & Gould, P.C.

(57) ABSTRACT

The invention concerns a method for the prevention or treatment of inflammatory bowel disease by administering an interferon-γ inhibitor. The invention further concerns pharmaceutical compositions and bispecific molecules useful in such method.

28 Claims, 7 Drawing Sheets

OTHER PUBLICATIONS

MacDonald, T.T. et al., "Tumour necrosis factor–alpha and interferon gamma production measured at the single cell level in normal and inflamed human intestine", *Clin. Exp. Immunol. 81*: 301–305 (1990).

Magazine and Johnson, "Characterization of a Synthetic Peptide Corresponding to a Receptor Binding Domain of Mouse Interferon", *Biochemistry 30*: 5784–5789 (1991).

Mahida, Y.R. et al., "Enhanced production of interleukin 1–$\beta$ by mononuclear cells isolated from mucosa with active ulcerative colitis of Crohn's disease", *Gut 30*: 835–838 (1989).

Podolsky, D.K., "Inflammatory Bowel Disease (First of Two Parts)", *New England J. Med. 325*, 928–937 (1992).

Rognum, T.O. et al., "Immunohistochemical evaluation of carcinoembryonic antigen, secretory component, and epithelial IgA in ulcerative colitis with dysplasia", *Gut 23*, 123–133 (1982).

Samudzi, C. T. et al., "Crystal structure of recombinant rabbit interferon–$\gamma$ at 2.7–Å Resolution", *J. Biol. Chem. 266*(32):21791–21797 (1991).

Selby, W.S. et al., "Expression of HLA–DR antigens by colonic epithelium in inflammatory bowel disease", *Clin. exp. Immunol. 53*, 614–618 (1983).

Dembic et al., "Prevention of streptozotocin induced diabetes in mice with the IFN–65 receptor immunoadhesions", abstract No. P7–3, 1992 ISIR Meeting Annual Mtg on the Interferon System, Toronto, Ontario, Canada, Sep. 28–Oct. 2, 1992, *J. of Interferon Research*, Mary Ann Liebert, Inc., Pubs.

Ozmen et al., "Effect of soluble MoIFN$\gamma$–R treatment of the development on spontaneous autoimmune disease in NZB/W F1 mice", abstract No. 5.19, 1992 ISIR Meeting Annual Mtg on the Interferon System, Toronto, Ontario, Canada, Sep. 28–Oct. 2, 1992, *J. of Interferon Research*, Mary Ann Liebert, Inc., Pubs.

Snapper & Paul, "Interferon–$\gamma$ and B Cell Stimulatory Factor–1 Reciprocally Regulate Ig Isotype Production", *Science 236*:944–947 (1987).

Zu & Jay, "The $E_1$ functional epitope of the human interferon $\gamma$ is a nuclear targeting signal–like element", *J. Biol. Chem. 266*(10):6023–6026 (1991).

Lunn, C. A. et al., "An active covalently linked dimer of human interferon–$\gamma$", *J. Biol. Chem. 267*:17920–17924 (1992).

Fais et al., "Spontaneous Release of Interferon $\gamma$ by Intestinal Lamina Propria Lymphocytes in Crohn's Disease. Kinetics of In Vitro Response to Interferon $\gamma$ Inducers," *Gut 32*: 403–407 (1991).

Harris et al., "Therapeutic Antibodies —the Coming of Age," *Tibtech 11*: 42–44 (1993).

Kuerschner, "Interferon–$\gamma$ Receptor/Immunoglobulin in Hybrid Molecules as Inhibitors of IFN$\gamma$ Function," *J. Interferon Res. 11*(Suppl. 1): s62 (ISR Meeting, Nov. 3–8, 1991).

Rhein et al., "Another Sepsis Drug Down—Immunex' TNF Receptor," *Biotechnology Newswatch*, Oct. 4, 1993.

P. Brandtzaeg et al., "The Mucosal Immune System in inflammatory System in inflammatory Bowel Disease," *Immunology and Medicine Series 19*: 19–39 (1992).

Byrn et al., "Biological properties of a CD4 immunoadhesin", *Nature 344*: 667–670 (1990).

Hodges et al., "Phase 1 Study of Recombinant Human CD4–Immunoglobulin in G Therapy of Patients with AIDS and AIDS–Related Complex", *Antimicrobial Agents & Chemotherapy* 35(22): 2580–2586 (1991).

Lionetti et al., "Activation of mucosal V$\beta$3+ T cells and tissue damage in human small intestine by the bacterial superantigen, *Staphyloccus aureus* enterotoxin B", *Eur. J Immunol., 23*:664–668 1993.

Murch et al., "Disruption of sulphated glycosaminoglycans in intestinal inflammation", *The Lancet, 341*: 711–714 (1993).

Kürschner, C. et al., "IFN$\gamma$, Receptor–Ig Fusion Proteins: Half–Life, Immunogenicity, and In Vivo Activity", *J. Immunol., 149*(12):4096–4100 (1992).

Yong et al., "$\gamma$–Interferon promotes proliferation of adult human astrocytes in vitro and reactive gliosis in the adult mouse brain in Vivo", *Proc. Natl. Acad. Sci., 88*: 7016–7020 (1991).

Raymond, C.A., "Diverse approaches to new therapies may hold promise in multiple sclerosis", *J. Am. Med. Assn., 256*(6): 685–687 (1986).

Didlake et al., "Effect of combined anti–gamma interferon antibody and cyclosporine therapy on cardiac allograft survival in the rat", *Transplantation, 45*:222–223 (1988).

Jacob et al., "In vivo treatment of (NZB × NZW)$F_1$ lupus–like nephritis with monoclonal antibody to $\gamma$ interferon", *J. Exp. Med., 166*:798–803 (1987).

Billiau, A., "Gamma–interferon: the match that lights the fire?", *Immunology Today, 9*: 37–40 (1988).

Heremans et al., "Interferon $\gamma$, a mediator of lethal lipopolysaccharide–induced shwartzman–like shock reactions in mice", *J. Exp. Med., 171*: 1853–1869 (1990).

MacDonald & Spencer, "Cell–mediated immune injury in the intestine", *Gastroenterology Clinics of North America, 21*(2): 367–386 (1992).

Haak–Frendscho et al., "Inhibition of interferon–$\gamma$ by an interferon–$\gamma$ receptor immunoadhesin", *Immunology, 79*: 594–599 (1993).

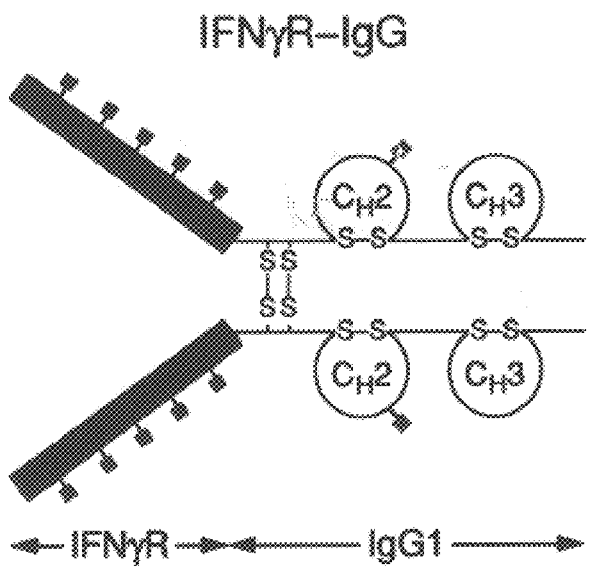
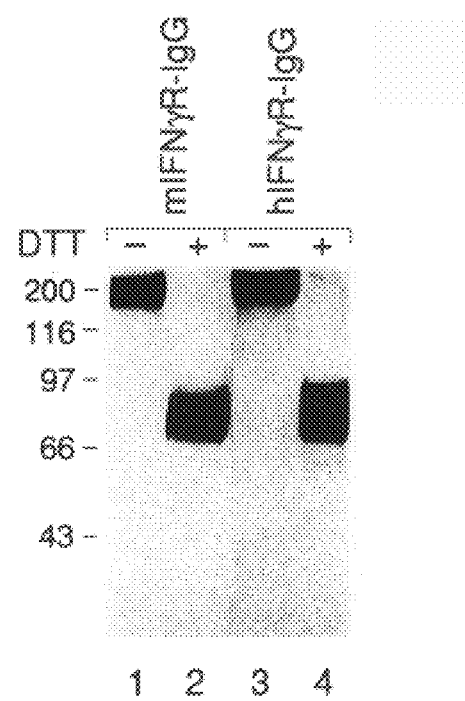
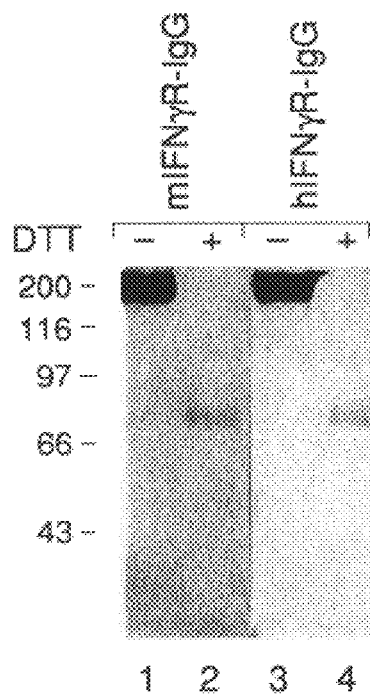
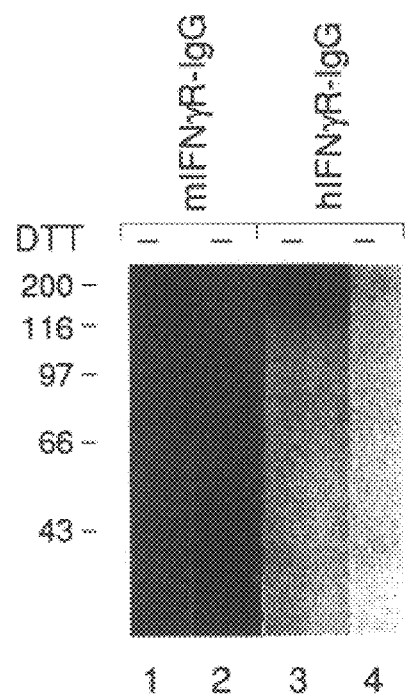
FIG. 1A
FIG. 1B
FIG. 1C
FIG. 1D

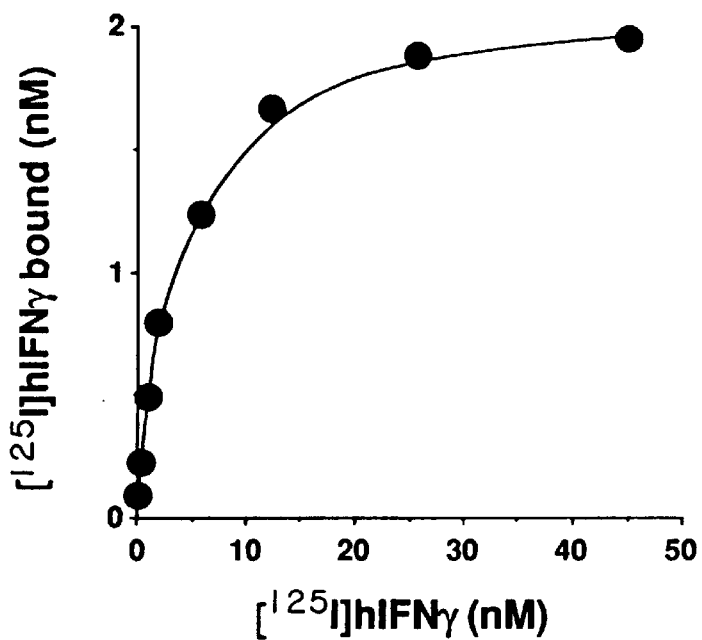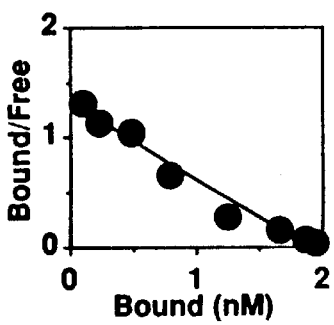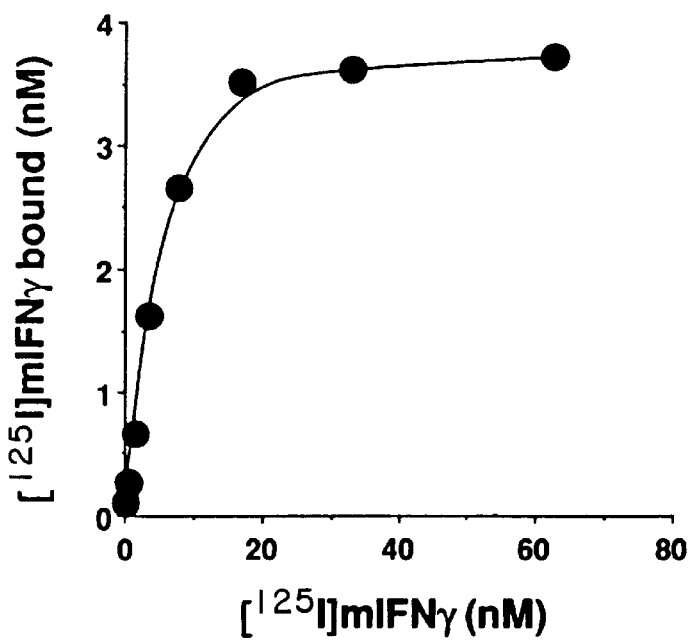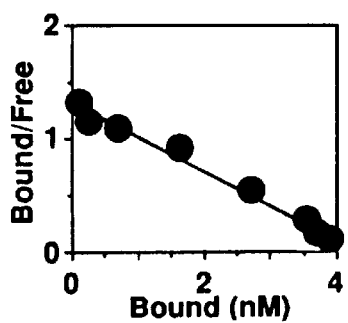

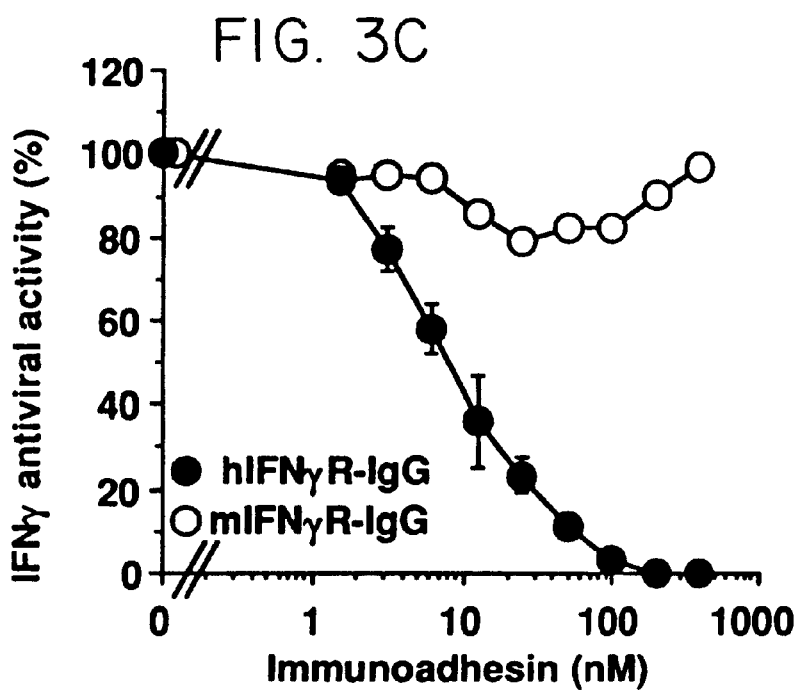
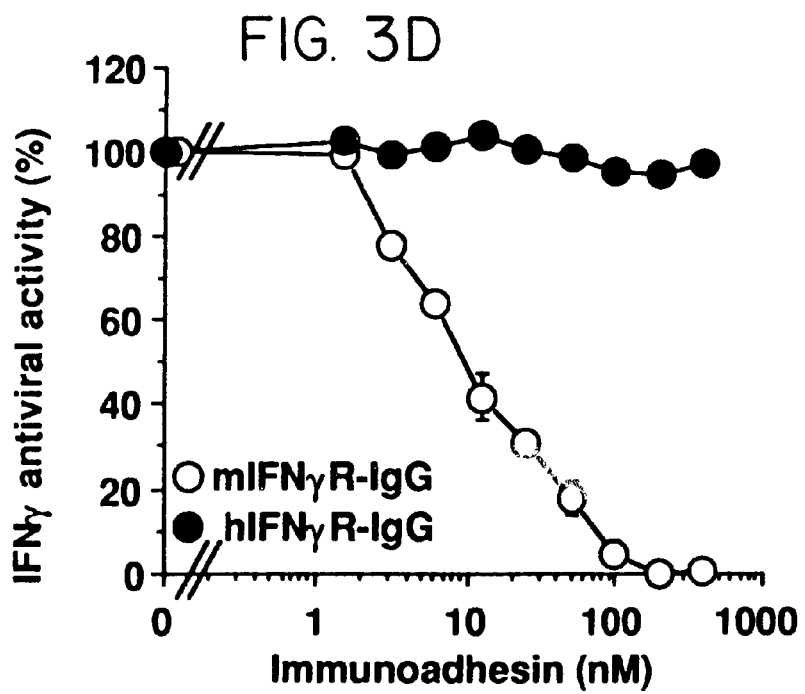

FIG. 6

```
                                                                    1
                                                                    MetAlaLeuLeuPheLeuLeuProLeuValMetGlnGlyValSerArgAla
   1 GAATTCCGCAGGCGCTCGGGGTTGGAGCCAGCGACCGTCGGTAGCAGCATGGCTCTCCTCTTTCTCCTACCCCTTGTCATGCAGGGTGTGAGCAGGGCT
                    20  ·                            ·                         40  ·
      GluMetGlyThrAlaAspLeuGlyProSerSerValProThrProThrAsnValThrIleGluSerTyrAsnMetAsnProIleValTyrTrpGluTyr
 100 GAGATGGGCACCGCGGATCTGGGGCCGTCCTCAGTGCCTACACCAACTAATGTTACAATTGAATCCTATAACATGAACCCTATCGTATATTGGGAGTAC
                                 ·             60  ·                                              80  ·
      GlnIleMetProGlnValProValPheThrValGluValLysAsnTyrGlyValLysAsnSerGluTrpIleAspAlaCysIleAsnIleSerHisHis
 199 CAGATCATGCCACAGGTCCCTGTTTTTACCGTAGAGGTAAAGAACTATGGTGTTAAGAATTCAGAATGGATTGATGCCTGCATCAATATTTCTCATCAT
                                                                100  ·
      TyrCysAsnIleSerAspHisValGlyAspProSerAsnSerLeuTrpValArgValLysAlaArgValGlyGlnLysGluSerAlaTyrAlaLysSer
 298 TATTGTAATATTTCTGATCATGTTGGTGATCCATCAAATTCTCTTTGGGTCAGAGTTAAAGCCAGGGTTGGACAAAAAGAATCTGCCTATGCAAAGTCA
                   120  ·                           ·                         140  ·
      GluGluPheAlaValCysArgAspGlyLysIleGlyProProLysLeuAspIleArgLysGluGluLysGlnIleMetIleAspIlePheHisProSer
 397 GAAGAATTTGCTGTATGCCGAGATGGAAAAATTGGACCACCTAAACTGGATATCAGAAAGGAGGAGAAGCAAATCATGATTGACATATTTCACCCTTCA
                                               160  ·                                            ·    180  ·
      ValPheValAsnGlyAspGluGlnGluValAspTyrAspProGluThrThrCysTyrIleArgValTyrAsnValTyrValArgMetAsnGlySerGlu
 496 GTTTTTGTAAATGGAGACGAGCAGGAAGTCGATTATGATCCCGAAACTACCTGTTACATTAGGGTGTACAATGTGTATGTGAGAATGAACGGAAGTGAG
                                                                200  ·
      IleGlnTyrLysIleLeuThrGlnLysGluAspAspCysAspGluIleGlnCysGlnLeuAlaIleProValSerSerLeuAsnSerGlnTyrCysVal
 595 ATCCAGTATAAAATACTCACGCAGAAGGAAGATGATTGTGACGAGATTCAGTGCCAGTTAGCGATTCCAGTATCCTCACTGAATTCTCAGTACTGTGTT
                   220  ·                            ·                        240  ·
      SerAlaGluGlyValLeuHisValTrpGlyValThrThrGluLysSerLysGluValCysIleThrIlePheAsnSerSerIleLysGlySerLeuTrp
 694 TCAGCAGAAGGAGTCTTACATGTGTGGGGTGTTACAACTGAAAAGTCAAAAGAAGTTTGTATTACCATTTTCAATAGCAGTATAAAAGGTTCTCTTTGG
                                             260  ·                            ·                280  ·
      IleProValValAlaAlaLeuLeuLeuPheLeuValLeuSerLeuValPheIleCysPheTyrIleLysLysIleAsnProLeuLysGluLysSerIle
 793 ATTCCAGTTGTTGCTGCTTTACTACTCTTTCTAGTGCTTAGCCTGGTATTCATCTGTTTTTATATTAAGAAAATTAATCCATTGAAGGAAAAAAGCATA
                                                                300  ·
      IleLeuProLysSerLeuIleSerValValArgSerAlaThrLeuGluThrLysProGluSerLysTyrValSerLeuIleThrSerTyrGlnProPhe
 892 ATATTACCCAAGTCCTTGATCTCTGTGGTAAGAAGTGCTACTTTAGAGACAAAACCTGAATCAAAATATGTATCACTCATCACGTCATACCAGCCATTT
                      320  ·                          ·                        340  ·
      SerLeuGluLysGluValValCysGluGluProLeuSerProAlaThrValProGlyMetHisThrGluAspAsnProGlyLysValGluHisThrGlu
 991 TCCTTAGAAAAGGAGGTGGTCTGTGAAGAGCCGTTGTCTCCAGCAACAGTTCCAGGCATGCATACCGAAGACAATCCAGGAAAAGTGGAACATACAGAA
                                              360  ·                                              380
      GluLeuSerSerIleThrGluValValThrThrGluGluAsnIleProAspValValProGlySerHisLeuThrProIleGluArgGluSerSerSer
1090 GAACTTTCTAGTATAACAGAAGTGGTGACTACTGAAGAAAATATTCCTGACGTGGTCCCGGGCAGCCATCTGACTCCAATAGAGAGAGAGAGTTCTTCA
                                                                400  ·
      ProLeuSerSerAsnGlnSerGluProGlySerIleAlaLeuAsnSerTyrHisSerArgAsnCysSerGluSerAspHisSerArgAsnGlyPheAsp
1189 CCTTTAAGTAGTAACCAGTCTGAACCTGGCAGCATCGCTTTAAACTCGTATCACTCCAGAAATTGTTCTGAGAGTGATCACTCCAGAAATGGTTTTGAT
                   420  ·                            ·                        440  ·
      ThrAspSerSerCysLeuGluSerHisSerSerLeuSerAspSerGluPheProProAsnAsnLysGlyGluIleLysThrGluGlyGlnGluLeuIle
1288 ACTGATTCCAGCTGTCTGGAATCACATAGCTCCTTATCTGACTCAGAATTTCCCCCAAATAATAAAGGTGAAATAAAAACAGAAGGACAAGAGCTCATA
                                              460  ·
      ThrValIleLysAlaProThrSerPheGlyTyrAspLysProHisValLeuValAspLeuLeuValAspAspSerGlyLysGluSerLeuIleGlyTyr
1387 ACCGTAATAAAAGCCCCCACCTCCTTTGGTTATGATAAACCACATGTGCTAGTGGATCTACTTGTGGATGATAGCGGTAAAGAGTCCTTGATTGGTTAT
                   480  ·                    489    ·
      ArgProThrGluAspSerLysGluPheSerEnd
1486 AGACCAACAGAAGATTCCAAAGAATTTTCATGAGATCAGCTAAGTTGCACCAACTTTGAAGTCTGATTTTCCTGGACAGTTTTCTGCTTTAATTTCATG

1585 AAAAGATTATGATCTCAGAAATTGTATCTTAGTTGGTATCAACCAAATGGAGTGACTTAGTGTACATGAAAGCGTAAAGAGGATGTGTGGCATTTTCAC

1684 TTTTGGCTTGTAAAGTACAGACTTTTTTTTTTTTTAAACAAAAAAAGCATTGTAACTTATGAACCTTTACATCCAGATAGGTTACCAGTAACGGAACA

1783 TATCCAGTACTCCTGGTTCCTAGGTGAGCAGGTGATGCCCCAGGGACCTTTGTAGCCACTTCACTTTTTTTCTTTTCTCTGCCTTGGTATAGCATATGT

1882 GTTTTGTAAGTTTATGCATACAGTAATTTTAAGTAATTTCAGAAGAAATTCTCGAAGCTTTTCAAAATTGGACTTAAAATCTAATTCAAACTAATAGAA

1981 TTAATGGAATATGTAAATAGAAACGTGTATATTTTTTATGAAACATTACAGTTAGAGATTTTTAAATAAAGAATTTTAAAACTCAAAAAAAAAAAAAAA

2080 AAAAAAAAAAAAAAAGGAATTC
```

TREATMENT OF INFLAMMATORY BOWEL DISEASE WITH IFN-γ INHIBITORS

This application is a 35 U.S.C. §371 application of International Patent Application No. PCT/US93/11966 filed Dec. 9, 1993, now inactive, which is a continuation-in-part application of U.S. Ser. No. 07/997,835 filed Dec. 29, 1992, now abandoned, to which application priority is claimed under 35 U.S.C §§120 and 365.

BACKGROUND OF THE INVENTION

I. Field of the Invention

The invention concerns the prevention or treatment of inflammatory bowel disease by administering an interferon-gamma (IFN-γ) inhibitor.

II. Description of Background and Related Art

Inflammatory bowel disease (IBD) is a collective term for ulcerative colitis (UC) and Crohn's disease, which are considered as two different entities, but have many common features and probably share at least some pathologic mechanisms. There is sufficient overlap in the diagnostic criteria for UC and CD that it is sometimes impossible to say which a given patient has; however, the type of lesion typically seen is different, as is the localization. UC mostly appears in the colon, proximal to the rectum, and the characteristic lesion is a superficial ulcer of the mucosa; CD can appear anywhere in the bowel, with occasional involvement of stomach, esophagus and duodenum, and the lesions are usually described as extensive linear fissures.

The aetiology of these diseases is unknown and the initial lesion has not been clearly defined; however, patchy necrosis of the surface epithelium, focal accumulations of leukocytes adjacent to glandular crypts, and an increased number of intraepithelial lymphocytes and certain macrophage subsets have been described as putative early changes, especially in Crohn's disease.

The current therapy of IBD usually involves the administration of antiinflammatory or immunosuppressive agents, such as sulfasalazine, corticosteroids, 6-mercaptopurine/azathioprine, or cyclosporine, which usually bring only partial results. If antiinflammatory/immunosuppressive therapies fail, colectomies are the last line of defense. About 30% of CD patients will need surgery within the first year after diagnosis. In,the subsequent years, the rate is about 5% per year. Unfortunately, CD is characterized by a high rate of recurrence; about 5% of patients need a second surgery each year after initial surgery. In UC, a further reason for resorting to surgery is that the patients are known to be at much increased risk for developing colorectal cancer, starting 10–15 years after the diagnosis of ulcerative colitis. Presumably this is due to the recurrent cycles of injury to the epithelium, followed by regrowth, increasing the risk of transformation. Accordingly, colostomy is used as prophylaxis against the development of cancer in UC patients.

IBD is rather common, with a prevalence that is claimed to be in the range of 70–170 in a population of 100,000. In view of the apparent shortcomings of the present treatments, there is a great medical need for a non-surgical approach, based upon a better understanding of the immunological reasons underlying this disorder.

A recent review of the characteristics of the mucosal immune system in IBD is by Brandtzaeg, P. et al. on pages 19–40 in Immunology of Gastrointestinal Disease, MacDonald, T. T. ed., Immunology and Medicine Series, Volume 19, Kluwer Academic Publishers, 1992.

Several attempts have been made to identify factors instrumental in the initiation of IBD; there have been reports on a genetically determined mucin defect in UC, and increased intestinal permeability and/or defective mucosal IgA system in Crohn's disease. There have further been persistent attempts to identify infectious agents associated with either UC or CD, with not much success. According to a recent, rather controversial theory, CD may be a vascular disease, characterized by localized tendency to thrombus formation leading to multifocal intestinal infarction and thereby causing the occurrence of early lesions. Altogether, the nature of the initial insult(s) resulting in IBD remains to be identified. However, there is considerable evidence that hyperactivation of the mucosal immune system in the gut through various immunopathological mechanisms may cause established IBD lesions.

The gut immune system is special in that the gut must absorb a vast amount of potentially antigenic material (food proteins) without reacting to any of it, and must control reactions to non-pathogenic organisms such as normal gut flora without losing the ability to react to abnormal, replicating organisms. The regulatory mechanisms that allow this kind of selective response are almost completely unknown. It is also unclear whether IBD results from an appropriate immune response to an abnormally persistent antigen, or an inappropriate response to a normal antigen.

The major lymphocytic tissues in the small intestine are the so called Peyer's patches (PP). Unlike the lymph node, PP do not have a capsule of afferent lymphatics. The epithelium over the PP lacks the crypts and villi of normal gut epithelium and is referred to as follicle-associated epithelium (FAE) containing cells called M cells. These are the major route of antigen transfer into the PP, and allow for direct sampling of antigen from the gut lumen by pinocytosis. Antigen is transported from the epithelium and presented to immunocompetent B cells, macrophages and dendritic cells in the underlying area. The colon has similar lymphoid arrangements called the lymphoid follicles. Lymphoid follicles are not identical to PP, but also have specialized epithelium containing M cells, and probably function as antigen presenting sites.

Underneath the epithelium there is a tissue called the lamina propria which forms the core of the villus and is densely infiltrated with lymphocytes bearing homing receptors which selectively bind to the mucosal lymphoid high endothelium. B cells comprise about 50% of the lymphocytes in the lamina propria of the gut, whereas the other half of lymphocytes are CD3+ T cells most of which are also CD4+. In the normal intestine, most of the B cells in the lamina propria are IgA+, although IgM-, IgG- and IgD-expressing cells are also found. Most of the immunoglobulin secreted into the intestine is IgA, and half of that is IgA-2, in contrast to the lymph nodes where most of the secreted IgA is of the IgA-1 isotype. The abundance of IgA antibodies is probably crucial for immunological homeostasis within the lamina propria. IgA antibodies lack potent effector functions such as complement activation, and may therefore block non-specific biological amplification mechanisms triggered by locally produced or serum-derived IgG antibodies.

As already mentioned, CD3+ T cells comprise approximately half of the lymphocytes in the lamina propria. This phenotype is also prevalent in human PP, and specifically in the interfollicular zones surrounding the high endothelial venules (HEV). In contrast, CD8+ T lymphocytes are predominant in the epithelium of humans.

Although it is not clear how inductive and suppressive immunoregulatory mechanisms are achieved in the gut, the lamina propria and epithelium, along with the organized lymphoepithelial nodules and the larger lymphoid aggregates, e.g. PP, are probably all involved in a complex manner.

The established mucosal IBD lesions are dominated by immunoglobulin-producing cells, both in UC and in CD. However, while the IgA- and IgM-expressing cell populations only increase several times as compared to normal mucosa, there is a disproportionate rise in the number of IgG-producing immunocytes. The actual number depends on the severity of the disease, but both UC and CD are characterized by a dramatically increased IgG production, including selective increases in the levels of specific IgG isotypes in both the intestinal mucosa and peripheral blood, and consequently by a remarkable decrease in the IgA/IgG ratio [MacDermott, R. P. et al., *Gastroenterology* 96, 764–768 (1989)].

It has been tentatively suggested that the selective increase in the production of IgG might reflect an immune response to one or several antigens, as well as the balance of cytokines and other regulatory factors, such as transforming growth factor β (TGF-β), that modulate immunoglobulin production in different populations of B cells [Podolsky, D. K., *New England J. Med.* 325, 928–937 (1992)]; however, there is no satisfactory explanation for this phenomenon as of yet.

Changes in the major subsets of the T cells population have also been observed in IBD. In CD, there is evidence that there are more memory cells than normal (lacking the CD45RA marker) and increased IL-2R expressing (activated) cells. CD4+ T-cells in the lamina propria seem to be increased relative to CD8+ T-cells in UC. It has been observed that the expression of certain cytokines is increased in IBD. This includes increased expression of interleukin-1 (IL-1), interleukin-6 (IL-6), altered expression of interleukin-2 (IL-2) and its receptor in both tissue and the circulation [Mahida, Y. R. et al., *Gut* 30, 838–838 (1989); Kusugami, K. et al., *Gastroenterology* 97, 1–9 (1989); Ligumsky, M. eta/., *Gut* 31, 686–689 (1990)]. Curiously, lower levels of IL-2 and IL-2 receptors have been reported in tissue from certain patients diagnosed with CD (Kusugami et al., supra). An IL-1 receptor antagonist has been described to reduce the severity of inflammation in a rabbit model of colitis [Cominelli, F. et al., *J. Clin. Invest.* 86, 972–980 (1990)]. A remarkably intensified epithelial expression of human leukocyte antigen complex DR (HLA-DR) in both UC and CD has led to the proposal that various cytokines are released locally from activated T cells [Selby, W. S. et al., *Clin. Exp. Immunol.* 53, 614–618 (1983); Brandtzaeg, P. et al. *Ann. Gastroenterol. Hepatol.* 21, 201–220 (1985); Rognum, T. O. et al., *Gut* 23, 123–133 (1982); Fais, S. et al., *Clin. Exp. Immunol.* 605–612 (1987)]. Although both IFN-γ and tumor necrosis factor α (TNF-α) are capable of enhancing epithelial HLA-DR on intestinal epithelium, difficulties have been encountered in demonstrating the production of IFN-γ in the IBD lesion [MacDonald, T. T. et al., *Clin. Exp. Immunol.* 81, 301–305 (1990)]. On the other hand, a raised number of cells producing TNF-α has been observed for both UC and CD lesions (MacDonald et al., supra).

In conclusion, whereas the relatively reduced IgA production and the striking increase of IgG-producing cells in IBD may reflect the establishment of a local immune defense mechanism, the causative factors for these changes have not yet been determined. Similarly, despite suggestions that certain cytokines and cytokine receptors may play a role in the development of IBD, their individual roles and complex interactions are not well. understood.

It is an object of the invention to provide a method for the prophylaxis or treatment of inflammatory bowel disease (IBD), including ulcerative colitis (UC) and Crohn's disease (CD).

It is a further object to provide bispecific molecules comprising an IFN-γ inhibitor and a further specificity to a target involved in the initiation or development of IBD.

It is yet another object to provide a method for the use of IFN-γ inhibitors in the preparation of pharmaceutical compositions suitable for the prophylaxis or treatment of disorders that involve a reduction in the percentage of IgA-producing immunocytes, such as IBD.

These and further objects of the present invention will be apparent for one skilled in the art.

SUMMARY OF THE INVENTION

The present invention is based on the premise that increased production of IFN-γ is instrumental in the inflammation, increased expression of HLA-DR on epithelia, and the change of IgA:IgG ratios in the gut in IBD patients. IFN-γ probably reduces the relative amount of immunoglobulin of the IgA subtype by selective killing of IgA-producing B cells, in particular CD5+ B cells, which constitute about 50% of the IgA-expressing B cells in the gut; it is, however, not intended to be bound by this or by any other theory.

In one aspect, the invention concerns a method comprising administering to a patient having or at risk of developing an inflammatory bowel disease, such as ulcerative colitis or Crohn's disease, a therapeutically or preventatively effective amount of an IFN-γ inhibitor. The IFN-γ inhibitor may, for example, be an amino acid sequence from an anti-IFN-γ antibody, an IFN-γ receptor polypeptide, an anti-IFN-γ receptor antibody, or an IFN-γ variant. The method includes the treatment of humans and non-human animals, such as mammals, rodents, etc.

In a particular embodiment, the IFN-γ inhibitor comprises the extracellular domain of an IFN-γ receptor, optionally fused to a stable plasma protein. The stable plasma protein preferably is an immunoglobulin, and the fusion preferably comprises at least a hinge region and the CH2 and CH3 domains of an immunoglobulin heavy chain.

In another aspect, the invention concerns a bispecific molecule comprising an IFN-γ inhibitor amino acid sequence and a further amino acid sequence capable of binding a target involved in the initiation or development of IBD. Just as before, the IFN-γ inhibitor may be an IFN-γ receptor, an anti-IFN-γ antibody, an anti-IFN-γ receptor antibody and an IFN-γ variant, and the further amino acid sequence preferably is from an IFN-γ inhibitor different from the one providing the first specificity, an IL-1 inhibitor, a TNF-α inhibitor, a CD11a/18 inhibitor, a CD11b/18 (VLA-4) inhibitor, or an L-selectin inhibitor.

In a specific embodiment, the bispecific molecule is a bispecific immunoadhesin.

In a further aspect, the invention concerns nucleotide sequences encoding the bispecific molecules of the invention, expression vectors containing such nucleotide sequences, recombinant host cells transformed with the expression vectors, and processes for culturing such host cells so as to express the encoded bispecific molecules.

In a still further aspect, the invention concerns the use of IFN-γ inhibitors in the preparation of pharmaceutical compositions for the prevention or treatment of disorders involving a reduction in the percentage of IgA-producing lymphocytes.

Production of IFN-γ at inappropriate levels, locations, or developmental stages has been implicated in the pathogenesis of several autoimmune and inflammatory diseases and in graft rejection. Thus, IFN-γ was present in newly diagnosed diabetic children and in muscle biopsies from patients with polymyosis. It has also found to cause exacerbation of autoimmune diseases such as multiple sclerosis and psoriasis. Anti-IFN-γ antibodies were shown to delay the development of a lupus-like disease with fatal immune-complex glomerulonephritis in mice, to inhibit endotoxin-induced lethality, and, alone or in combination with immunosuppressive agents, to inhibit allograft rejection. Fusion proteins consisting of the mouse IFN-γ receptor extracellular portion and constant domains of immunoglobulin molecules have been made and proposed as useful in the therapy for autoimmune diseases, chronic inflammation, delayed type of hypersensitivity and allograft rejection [Kurschner, C. et al., *J. Biol. Chem.* 267, 9354–9360 (1992); Dembic, Z et al., The 1992 ISIR Meeting of the Interferon System, Toronto, Ontario, Canada, Sep. 28–Oct. 2, 1992, *J. of Interferon Research* Vol. 12, suppl. Sep. 1, 1992, Abstract P7-3]. Nowhere has been proposed, however, that IFN-γ may play a major role in the development of IBD, and, as mentioned before, attempts to demonstrate the production of IFN-γ in IBD lesions were unsuccessful.

BRIEF DESCRIPTION OF THE DRAWINGS

FIG. 1A is a schematic depiction of the structure of IFNγR-IgG immunoadhesins. IFNγR (shaded bar) denotes the extracellular portion of the human or murine IFN-γ receptor and IgG-1 (thin line) denotes the hinge region and CH2 and CH3 constant domains of human IgG-1 heavy chain. Locations of putative N-linked glycosylation sites are shown (square boxes). FIGS. 1B–1D are images of SDS polyacrylamide electrophoresis gels/blots that depict the subunit structure of IFN-γ-IgG. HEK293 cells were transfected with a vector directing transient by expression of murine (lanes 1, 2) or human (lanes 3, 4) IFNγR-IgG. The protein was recovered from culture supernatants and purified by affinity chromatography on *S. aureus* protein A. SDS polyacrylamide electrophoresis was carried out without (−) or with (+) reduction by 10 mM dithiothreitol (DTT). The proteins were stained with Coomassie blue (FIG. 1B) or electroblotted onto introcellulose paper and incubated with (FIG. 1C) antibodies to human IgG Fc or with (FIG. 1D) murine (lanes 1, 2) or human (lanes 3, 4) [$^{125}$I]IFN-γ (10 nM) alone (lanes 1, 3), or with 1 µM unlabeled human or murine IFN-γ (lanes 2, 4). Blots were developed with horseradish peroxidase-conjugates second antibody and 4-chloronaphtot (FIG. 1C) or by autoradiography (FIG. 1D).

FIGS. 2A-1, 2A-2, 2B-1 and 2B-2 are graphs depicting the binding of IFNγR-IgG to IFN-γ. Human (FIGS. 2A-1 and 2A-2) or murine (FIGS. 2B-1 and 2B-2) IFNγR-IgG was immobilized in microtiter wells coated with anti-IgG Fc antibody and incubated with increasing concentrations of recombinant human or murine [$^{125}$I]IFN-γ, respectively. Scatchard analyses of the saturation data are shown in FIGS. 2A-2 and 2B-2. Nonspecific binding was determined by omitting the IFNγR-IgG and was typically less than 10% of the total binding. The data are from a representative experiment done in triplicate.

FIGS. 3A–3D are graphs depicting inhibition of IFN-γ by IFNγR-IgG in vitro. (FIG. 3A) inhibition of hIFN-γ induction of ICAM-1 expression in human HeLa cells by hIFNγR-IgG (closed circles). (FIG. 3B) Inhibition of mIFN-γ induction of the class I MHC antigen H2-K$^k$ in mouse L929 cells by mIFNγR-IgG (open circles). (FIG. 3C) Inhibition of hIFN-γ antiviral activity by hIFNγR-IgG as measured by survival of human A 549 cells infected by encephalomyocarditis virus (EMCV). (FIG. 3D) Inhibition of mIFN-γ antiviral activity by mIFNγR-IgG as measured by survival of mouse L929 cells infected by EMCV. The data in each panel are means ±SD from two experiments in which the nuwnber of replicates was 1 (FIGS. 3A and 3B) or 4 (FIGS. 3C and 3D). In each respective panel, CD4-IgG (open boxes) (FIGS. 3A and 3B), or mIFNγR-IgG (FIG. 3C), or hIFNγR-IgG (FIG. 3D) were used as negative controls.

FIG. 6 depicts the human IFN-γ receptor nucleotide (SEQ ID NO:1) and predicted amino acid sequences (SEQ ID NO:2).

DETAILED DESCRIPTION OF THE INVENTION

I. Definitions

Figure 3A:
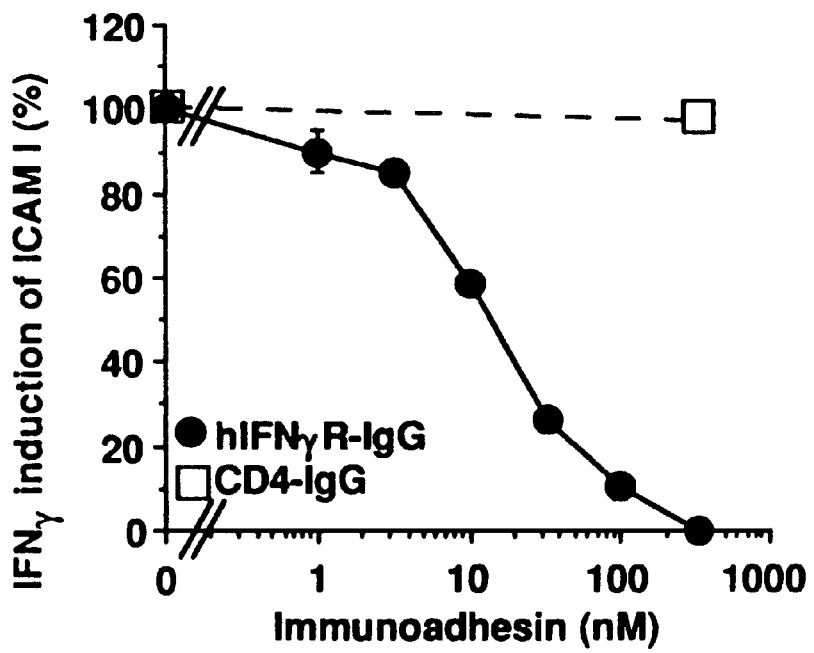

"Inflamnnatory bowel disease (IBD)" is used as a collective term for "ulcerative colitis (UC)" and "Crohn's disease (CD)". Although UC and CD are generally considered as two different entities, Their common characteristics, such as patchy necrosis of the surface epithelium, focal accumulations of leukocytes adjacent to glandular crypts, and an increased number of intraepithelial lymphocytes (IEL) and certain macrophage subsets, justify their treatment as a single disease group.

The term "reduction in the percentage of inmmunoglobulin A (IgA)" is used to refer to a decrease in The relative amount of antibodies of the IgA class in the patient's body, as compared to antibodies of other classes, i.e. IgG, IgM, IgD, IgE, in particular IgG, whether due to a reduction in the percentage of IgA-producing immunocytes or to their decreased ability to produce IgA, or to any other factor(s). IfThe condition to be treated is IBD, the reduction takes place within the gut.

Interferon gamma (IFN-γ), also known as immune interferon, is a member of the interferon family, which exhibits the antiviral and anti-proliferative properties characteristic of interferons-α and -β but, in contrast to those interferons, is pH 2 labile. IFN-γ was originally produced upon mitogenic induction of lymphocytes. The recombinant production of human IFN-γ was first reported by Gray, Goeddel and co-workers [Gray et al., *Nature* 295, 503–508 (1982)], and is subject of U.S. Pat. Nos. 4,762,791, 4,929,544, 4,727,138 and 4,925,793. The recombinant human IFN-γ of Gray and Goeddel as produced in *E. coli*, consisted of 146 amino acids, the N-terminal portion of the molecule commencing with the sequence CysTyrCys. It has later been found that the native human IFN-γ (i.e., that arising from mitogen induction of human peripheral blood lymphocytes and subsequent purification) is a polypeptide which lacks the CysTyrCys N-terminus assigned by Gray et al., Supra. A used herein, "interferon gamma" or "IFN-γ" refers variously to all forms of (human and non-human animal) interferon gamma as are known to be biologically active in accepted interferon gamma assays, such as by inhibition of virus replication in a suitable cell line (inhibition of encephalomyocarditis virus replication in human lung carcinoma cell line A549 for human IFN-γ), induction of class II antigens, heat lability, other antiviral, antitumor or immunoregulatory assays, or neutralization by antibodies having immunoreactivity for gamma interferon but not alpha- or beta-interferon, and is meant to include human interferon-γ in a mature, pro, met or des(1–3) (also referred to as desCysTyrCys IFN-γ) form, whether obtained from natural source, chemically synthesized or produced by techniques of recombinant DNA technology. A complete description of the preparation of recombinant human interferon gamma (hIFN-γ) including its cDNA and amino acid sequences is shown in the United States Patents cited hereinabove (e.g. U.S. Pat. No. 4,762,791). CysTyrCys-lacking recombinant human IFN-γ, including variously truncated derivatives are, for example, disclosed in European Publication No. 146,354. Non-human animal interferons, including animal, such as mammalian IFN-γ, are, for example, disclosed in European Publication No. 88,622. The term includes variously glycosylated forms and other variants and derivatives of such interferons, whether known in the art or will become available in the future. Examples of such variants are alleles, and the products of site directed mutagenesis in which residues are deleted, inserted and/or substituted (see, for example European Publication No. 146,354 referred to above).

The expressions "human interferon gamma", "human IFN-γ" and "hIFN-γ", which are used interchangeably, refer to a family of polypeptide molecules that comprise the full-length (146 amino acids) human IFN-γ of Gray et al., supra, the native human IFN-γ lacking the first three N-terminal amino acids of the full length species (desCysTyrCys human IFN-γ), and their amino acid sequence variants, provided that the nucleotide sequences encoding such variants are capable of hybridizing under stringent conditions with the complement of a nucleotide sequence encoding the native amino acid sequence, and that they retain the ability to exhibit IFN-γ biological action. This definition specifically includes human IFN-γ from natural sources, synthetically produced in vitro or obtained by genetic manipulation including methods of recombinant DNA technology. The amino acid sequence variants preferably share at least about 65% sequence homology, more preferably at least about 75% sequence homology, even more preferably at least about 85% sequence homology, most preferably at least about 90% sequence homology with any domain, and preferably with the receptor binding domain(s), of the native human IFN-γ amino acid sequence. The definition specifically covers variously glycosylated and unglycosylated forms of native human IFN-γ and of its amino acid sequence variants.

The expressions "native human interferon gamma", "native human IFN-γ" and "native hIFN-γ" are used to refer to the mature 143 amino acids native human IFN-γ that arises from mitogen induction of human peripheral blood lymphocytes and subsequent purification, and any naturally occurring fragment or derivative thereof provided that it exhibits IFN-γ biological action. This definition specifically includes naturally occurring alleles of IFN-γ.

The expressions "interferon gamma inhibitor" and IFN-γ inhibitor" are used interchangeably and refer to polypeptides or organic molecules capable of inhibiting the interaction of native IFN-γ with its receptor and thereby blocking the pathogenic effect of native IFN-γ in at least an in vitro model of inflammatory bowel disease, irrespective of the mechanism by which this inhibition is achieved. IFN-γ inhibitors specifically include molecules capable of inhibiting the binding of native IFN-γ to its native receptor, either by binding to native IFN-γ or by binding to a native IFN-γ receptor (IFN-γ antagonists), in a standard competitive binding assay. IFN-γ inhibitors blocking IFN-γ action by binding native IFN-γ include, but are not limited to, IFN-γ receptors, and (blocking) anti-IFN-γ antibodies. Alternatively, IFN-γ antagonists may act by binding but not activating a native IFN-γ receptor, such as certain IFN-γ derivatives and anti-IFN-γ receptor antibodies.

The term "inhibitor" is used in an analogous manner in relation to other molecules, such as cytokines, e.g. IL-1, or TNF-α; CD11a/18; CD1b/18 (VLA-4); L-selectin.

IFN-γ receptors have been purified from different human [Aguet, M. & Merlin, G., J. Exp. Med. 165, 988–999 (1987); Novick, D. et al., J. Biol. Chem. 262, 8483–8487 (1987); Calderon, J. et al., Proc. Natl. Acad. Sci. USA 85, 4837–4841 (1988)] and murine [Basu, M. et al., Proc. Natl. Acad. Sci. USA 85, 6282–6286 (1988)] cell types, and have been characterized as 90- to 95-kDa single chain integral membrane glycoproteins that display certain structural heterogeneity due to cell specific glycosylation. The primary sequence of human IFN-γ receptor has been elucidated by Aguet et al., Cell 55, 273–280 (1988), who cloned, expressed and sequenced a 2.1 kb human IFN-γ receptor cDNA from a Raju cell expression library prepared in λgt11. The cloning and expression of the cDNA for the murine interferon gamma (IFN-γ) receptor was reported by Gray, P. W. et al., Proc. Natl. Acad. Sci. USA 86, 8497–8501 (1989). The terms "interferon gamma receptor" and "IFN-γ receptor" are used interchangeably and refer to a family of polypeptide molecules that comprise any naturally occurring (native) IFN-γ receptor from any animal species, and amino acid sequence and glycosylation variants of such receptors, provided that the nucleotide sequences encoding such variants are capable of hybridizing, under stringent conditions, to the complement of a nucleotide sequence encoding a native IFN-γ receptor, and that they retain the ability to bind IFN-γ. The amino acid sequence variants preferably share at least about 65% sequence homology, more preferably at least about 75% sequence homology, even more preferably at least about 85% sequence homology, most preferably at least about 90% sequence homology with any domain, and preferably with the ligand binding domain(s), of a native IFN-γ receptor amino acid sequence from the same (human or non-human) animal species. IFN-γ receptors (occasionally referred to as IFN-γ binding proteins) are disclosed, e.g. in EP 240,975 published Oct. 14, 1987; EP 369,413 published May 23, 1990; EP 393,502 published Oct. 24, 1990; EP 416,652 published Mar. 13, 1991.

The expressions "human interferon gamma receptor" and "human IFN-γ receptor", which are used interchangeably, refer to a family of polypeptide molecules that comprise the full-length, native human IFN-γ receptor having the amino acid sequence shown in FIG. 6 and its amino acid sequence variants, provided that the nucleic acids encoding such variants are capable of hybridizing under stringent conditions with the complement of a nucleic acid encoding the native amino acid sequence, and that they retain the ability to bind IFN-γ. This definition specifically encompasses soluble forms of native full-length human IFN-γ receptor, from natural sources, synthetically produced in vitro or obtained by genetic manipulation including methods of recombinant DNA technology. The amino acid sequence variants preferably share at least about 65% sequence homology, more preferably at least about 75% sequence homology, even more preferably at least about 85% sequence homology, most preferably at least about 90% sequence homology with any domain, and preferably with the ligand (IFN-γ) binding domain(s), of the native full-length human IFN-γ receptor amino acid sequence. The definition specifically covers variously glycosylated and unglycosylated forms of any native human IFN-γ receptor and of its amino acid sequence variants.

The "stringent conditions" are overnight incubation at 42° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

The term "native human interferon gamma receptor" or "native human IFN-γ receptor" is used to refer to the mature full-length native human IFN-γ receptor as disclosed by Aguet et al., supra, and any naturally occurring fragment or derivative, such as allelic variant, thereof provided that it retains the ability to bind IFN-γ.

"Biologically active" IFN-γ variants, also referred to as variants exhibiting "IFN-γ biological activity" share an effector function of a naturally occurring IFN-γ molecule, which may, but need not, in addition possess an antigenic function. Effector functions include receptor binding, any anti-viral, anti-bacterial, cytotoxic, anti-tumor, or immuno-regulatory activity of a native IFN-γ molecule. The antigenic functions essentially mean the possession of an epitope or antigenic site that is capable of cross-reacting with antibodies raised against a naturally occurring IFN-γ molecule. Molecules inhibiting "IFN-γ biological activity" inhibit an effector function of IFN-γ.

The terms "amino acid" and "amino acids" refer to all naturally occurring L-α-amino acids. The amino acids are identified by either the single-letter or three-letter designations:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids
   Acidic Residues: aspartic acid, glutamic acid
   Basic Residues: lysine, arginine, histidine
II. Uncharged Amino Acids
   Hydrophilic Residues: serine, threonine, asparagine, glutamine
   Aliphatic Residues: glycine, alanine, valine, leucine, isoleucine
   Non-polar Residues: cysteine, methionine, proline
   Aromatic Residues: phenylalanine, tyrosine, tryptophan The term "amino acid sequence variant" refers to molecules with some differences in their amino acid sequences as compared to a native amino acid sequence.

"Homology" is defined as the percentage of residues in the candidate amino acid sequence that are identical with the residues in the amino acid sequence of their native counterparts after aligning the sequences and introducing gaps, if necessary, to achieve the maximum percent homology. Methods and computer programs for the alignment are well known in the art.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the a-carboxy or a-α mino functional group of the amino acid.

Deletional variants are those with one or more amino acids in the native amino acid sequence removed. Ordinarily, deletional variants will have one or two amino acids deleted in a particular region of the molecule.

The term "glycosylation variant" is used to refer to a glycoprotein having a glycosylation profile different from that of a native counterpart. Glycosylation of polypeptides is typically either N-linked or O-linked. N-linked refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation. Any difference in the location and/or nature of the carbohydrate moieties present in an IFN-γ receptor protein as compared to its native counterpart is within the scope herein.

"Stable plasma proteins" are proteins typically having about 30 to about 2000 residues, which exhibit in their native environment an extended half-life in the circulation, i.e. a half-life greater than about 20 hours. Examples of suitable stable plasma proteins are immunoglobulins, albumins (such as human serum albumin, HSA), lipoproteins, apolipoproteins and transferrin.

Antibodies (Abs) and immunoglobulins (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains [Clothia et al., *J. Mol. Biol.* 186, 651–663 (1985); Novotny and Haber, *Proc. Natl. Acad. Sci. USA* 82, 4592–4596 (1985)].

The variability is not evenly distributed through the variable regions of antibodies. It is concentrated in three segments called complementarity determining regions (CDRs) or hypervariable regions both in the light chain and the heavy chain variable regions. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies [see Kabat, E. A. et al., *Sequences of Proteins of Immunolooical Interest* National Institute of Health, Bethesda, Md. (1987)]. The constant domains are not involved directly in binding an antibody to an antigen, but exhibit various effector functions, such as participation of the antibody in antibody-dependent cellular toxicity.

Papain digestion of antibodies produces two identical antigen binding fragments, called Fab fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$–$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab' fragments differ from Fab fragments by the addition of a few residues at the carboxy terminus of the heavy chain $C_H1$ domain including one or more cysteines from the antibody hinge region. Fab'—SH is the designation herein for Fab' in which the cysteine residue(s) of the constant domains bear a free thiol group. F(ab')$_2$ antibody fragments originally were produced as pairs of Fab' fragments which have hinge cysteines between them. Other, chemical couplings of antibody fragments are also known.

The light chains of antibodies (immunoglobulins) from any vertebrate species can be assigned to one of two clearly distinct types, called kappa and lambda (λ), based on the amino acid sequences of their constant domains.

Depending on the amino acid sequence of the constant region of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant regions that correspond to the different classes of immunoglobulins are called α, delta, epsilon, γ, and μ, respectively. The subunit structures and three-dimensional configurations of different classes of immunoglobulins are well known. IgA-1 and IgA-2 are monomeric subclasses of IgA, which usually is in the form of dimers or larger polymers. Immunocytes in the gut produce mainly polymeric IgA (also referred to poly-IgA including dimers and higher polymers). Such poly-IgA contains a disulfide-linked polypeptide called the "joining" or "J" chain, and can be transported through the glandular epithelium together with the J-chain-containing polymeric IgM (poly-IgM), comprising five subunits.

The term "antibody" is used herein in the broadest sense and specifically covers single monoclonal antibodies, immunoglobulin chains or fragments thereof, which react immunologically with a corresponding polypeptide, such as IFN-γ or an IFN-γ receptor as well as anti-IFN-γ and anti-IFN-γ receptor antibody compositions with polyepitopic specificity, which have such properties.

The term "monoclonal antibody" as used herein refers to an antibody (as hereinabove defined) obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins.

"Humanized" forms of non-human (e.g. murine) antibodies are immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance.

The phrase "bispecific molecule" is used to define a polypeptide with two specificities. The amino acid sequences providing the two specificities ("binding domains") may be directly fused to each other or may be connected with a "linker". The linker may be the residue of a covalent cross-linking agent capable of linking the two binding domains without the impairment of their ability to bind their respective native receptors or ligands or a linkage the formation of which is induced by such cross-linking agents. A concise review of covalent cross-linking reagents, including a guide to the selection of such reagents and methods for their preparation are provided by Tae, H. Jr. in *Meth. Enzymol.* 580–609 (1983) and in the references cited therein. The selection of the most appropriate reagent for a specific purpose from the wide variety of cross-linking agents available, is well within the skill of an ordinary artisan. In general, zero-length, homo- or heterobifunctional cross-linking agents are preferred for making the bispecific molecules of the present invention. Zero-length cross linking reagents induce the direct conjugation of two binding domains without the introduction of any extrinsic material. Agents that catalyze the formation of disulfide bonds belong in this category. Another example is reagents that induce the condensation of carboxy and primary amino groups to form an amide bond, such as carbodiimides, ethylchloroformate, Woodward's reagent K1, carbonyldiimidazole, etc. Homobifunctional reagents carry two identical functional groups, whereas heterobifunctional reagents contain two dissimilar functional groups. A vast majority of the heterobifunctional cross-linking agents contains a primary amine-reactive group and a thiol-reactive group. A novel heterobifunctional linker for formyl to thiol coupling was disclosed by Heindel, N. D. et al., *Bioconiuqate Chem.* 2, 427–430 (1991)]. In a preferred embodiment, the covalent cross-linking agents are selected from reagents capable of forming disulfide (—S—S—), glycol (—CH[OH]—CH[OH]—), azo (—N=N—), sulfone (—S[=O$_2$]—), or ester (—C[=O]—O—) bridges. In a different approach, the binding domains are linked via their oligosaccharides. Chemical or enzymatic oxidation of oligosaccharides on polypeptide ligands to aldehydes yields unique functional groups on the molecule, which can react with compounds containing, for example, amines hydrazines, hydrazides, or semicarbazides. Since the glycosylations sites are well defined in polypeptide molecules, selective coupling via oxidized oligosaccharide moieties will yield in a more uniform product than other coupling methods, and is expected to have less adverse effect on the receptor binding properties of the ligands. A carbohydrate-directed heterobifunctional cross-linking agent, 4-(4-N-maleimidophenyl)butyric acid hydrazide.HCl (MPBH), was, for example, described by Chamow et al., *J. Biol. Chem.* 267, 15916–15922 (1992). MPBH can be purchased from the Pierce Chemical Company, Rockford, Ill. (Product #22302), along with other reagents of similar structures, such as 4-(N-maleimidomethyl)cyclohexan-1)carboxyl hydrazide.HCl (M$_2$C$_2$H; Product #22304), and 3-(2-pyridylthio)propionyl hydrazide (PDPH; Product #2230). It will be understood that the coupling of more than two binding sequences with various linked sequences, e.g., cross-linking reagents is possible, and is within the scope of the present invention.

In a further embodiment, in the bispecific molecules of the present invention the binding domains are connected by polypeptide linker sequences, and accordingly, are presented to their receptor/ligand as a single-chain multifunctional polypeptide molecule. The polypeptide linker functions as a "spacer" whose function is to separate the functional binding domains so that they can independently assume their proper tertiary conformation. The polypeptide linker usually comprises between about 5 and about 25 residues, and preferably contains at least about 10, more preferably at least about 15 amino acids, and is composed of amino acid residues which together provide a hydrophilic, relatively unstructured region. Linking amino acid sequences with little or no secondary structure work well. If desired, one or more unique cleavage sites recognizable by a specific cleavage agent (e.g. protease) may be included in the polypeptide linker. The specific amino acids in the spacer can vary, however, cysteines should be avoided. The spacer sequence may mimic the tertiary structure of an amino acid sequence normally linking two receptor binding domains in a native bifunctional ligand. It can also be designed to assume a desired structure, such as a helical structure. Suitable polypeptide linkers are, for example, disclosed in WO 88109344 (published Dec. 1, 1988), as are methods for the production of multifunctional proteins comprising such linkers.

In a further specific embodiment, the binding domains are connected by amphiphilic helices. It is known that recurring copies of the amino acid leucine (Leu) in gene regulatory proteins can serve as teeth that "zip" two protein molecules together to provide a dimer. Leucine zipper was first discovered when a small segment of the protein C/EBP was fit into a hypothetical alpha helix. Surprisingly, the leucines, which make up every seventh amino acid in this protein, lined up in a column. Subsequently, two additional, C/EBP related proteins were identified and shown to have a similar function. One of them, GCN4 is a gene regulatory protein from yeast, the other one, is the product of a proto-oncogene jun. It has been found that zipper regions associate in parallel when they combine, i.e. the leucines on apposed molecules line up side by side. It has also been shown that non-identical proteins may be zippered to provide heterodimers. Such leucine zippers are particularly suitable for preparing bispecific molecules within the scope of the invention. Alternatively, the sequence of the amphipathic helix may be taken from a four-helix bundle design, essentially as described by Pack P. and Pluckthun, A., *Biochemistry* 31, 1579–1584 (1992). For further details about molecular, e.g. leucine zippers, which can serve as linkers for the purpose of the present invention, see for example: Landshculz, W. H., et al. *Science* 240, 1759–1764(1988); O'Shea, E. K. et al., *Science* 243, 538–542 (1989); McKnight, S. L., *Scientific American* 54–64, April 1991; Schmidt-Dorr. T. et al., *Biochemistry* 30, 9657–9664 (1991); Blondel, A. and Bedouelle, H. *Protein Engineering* 4, 457–461 (1991), Pack, P. and Pluckthun, A., supra, and the references cited in these papers.

In a preferred embodiment, the linker comprises an immunoglobulin sequence preferably resulting in a bispecific immunoadhesin.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e. is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesins may be obtained from any immunoglobulin, such as IgG-1, IgG-2, IgG-3, or IgG-4 subtypes, IgA (including IgA-1 and IgA-2), IgE, IgD or IgM.

As used herein the phrase "bispecific immunoadhesin" designates immunoadhesins having at least two binding specificities, one of which may be an antigen binding site of an antibody. Bispecific immunoadhesins can generally be assembled as hetero-multimers, and particularly as heterodimers, -trimers or -tetramers, essentially as disclosed in WO 89/02922 (published Apr. 6, 1989) or in EP 314,317 (published May 3, 1989). Whereas the binding domains providing the two desired specificities in the bispecific molecules of the present invention preferably replace the variable domains of immunoglobulins, they can also be inserted between immunoglobulin heavy chain and light chain sequences such that an immunoglobulin comprising a chimeric heavy chain is obtained. In this embodiment, the binding sequences are fused to the 3' end of an immunoglobulin heavy chain in each arm of an immunoglobulin, either between the hinge and the CH2 domain, or between the CH2 and CH3 domains. Similar constructs have been reported by Hoogenboom, H. R. et al., *Mol. Immunol.* 28, 1027–1037 (1991).

The term "bispecific antibody" is used herein to describe antibody molecules which comprise two different antigen binding sites. The bispecific antibodies may be assembled as hetero-multimers, and particularly as hetero-dimers, -trimers or tetramers, as hereinabove described for bispecific immunoadhesins.

The expression "immunoglobulin heavy chain constant domain sequence lacking a(n immunoglobulin) light chain binding site" is used to designate an immunoglobulin heavy chain constant domain sequence from which sequence elements to which the light chain is ordinarily linked are removed or sufficiently altered (mutated) so that such binding is no longer possible. In a preferred embodiment, the entire CH1 domain is deleted but shorter truncations of immunoglobulin constant domains are also suitable, provided that the section to which the light chain is ordinarily disulfide-bonded or interacts with non-covalently is removed. Alternatively, the light chain binding region of an immunoglobulin heavy chain constant domain may be mutated (by substitution or insertion) so that it is no longer capable of covalent or non-covalent binding to an immunoglobulin light chain.

The terms "nucleic acid molecule encoding", "DNA sequence encoding", and "DNA encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

Nucleic acid is "operably linked" when it is placed into a functional relationship with another nucleic acid sequence. For example, DNA for a presequence or secretory leader is operably linked to a DNA encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property as screened for in the originally transformed cell are included.

"Transformation" means introducing DNA into an organism so that the DNA is replicable, either as an extrachromosomal element or by chromosomal integration.

"Transfection" refers to the taking up of an expression vector by a host cell whether or not any coding sequences are in fact expressed.

The terms "transformed host cell" and "transformed" refer to the introduction of DNA into a cell. The cell is termed a "host cell", and it may be a prokaryotic or a eukaryotic cell. Typical prokaryotic host cells include various strains of *E. coli*. Typical eukaryotic host cells are mammalian, such as Chinese hamster ovary cells or human embryonic kidney 293 cells. The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA.

"Oligonucleotides" are short-length, single- or double-stranded polydeoxynucleotides that are chemically synthesized by known methods [such as phosphotriester, phosphite, or phosphoramidite chemistry, using solid phase techniques such as those described in EP 266,032, published May 4, 1988, or via deoxynucleoside H-phosphanate intermediates as described by Froehler et al., *Nucl. Acids Res.* 14, 5399 (1986)]. They are then purified on polyacrylamide gels.

"Ligation" refers to the process of forming phosphodiester bonds between two double stranded nucleic acid fragments (Maniatis et al., *Molecular Cloning: A Laboratory Manual* Cold Springs Harbor Laboratory, Cold Spring Harbor, 1982, p. 146). Unless otherwise stated, ligation may be accomplished using known buffers and conditions with 10 units of T4 DNA ligase ("ligase") per 0.5 $\mu$g of approximately equimolar amounts of the DNA fragments to be ligated. "Digestion" of DNA refers to catalytic cleavage of the DNA with an enzyme that acts only at certain locations in the DNA. Such "restriction enzymes" recognize specific "restriction sites". The various restriction enzymes used herein are commercially available, and their restriction conditions, cofactors and other requirements as established by the enzyme suppliers were used. In general, about 1 $\mu$g of plasmid or DNA fragment is used with about 2 units of enzyme in about 20 $\mu$l of buffer solution. Appropriate buffers and substrate amounts for particular restriction enzymes are specified by the manufacturer. Incubation times of about 1 hour at 37° C. are ordinarily used, but may very in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragments from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (Maniatis et al., Supra, pp. 133–134).

II. Availability of IFN-γ Inhibitors

A. Anti-IFN-γ and Anti-IFN-γ Receptor Antibodies

Anti-IFN-γ antibodies blocking various biological activities of native IFN-γ (often referred to as "neutralizing antibodies") are known in the art, and are, for example, disclosed in the following publications: Billiau, A., *Immunol. Today* 9, 37–40 (1988); Hereman, H. et al., *J. Exp. Med.* 171, 1853–1859 (1990); Landolfo, S. et al, *Science* 229, 176–179 (1985); Didlake, R. H. et al., *Transplantation* 45, 222–223 (1988), Jacob, C. O. et al., *J. Exo. Med.* 166, 789–803 (1987); Yong, V. W. et al., *Natl. Acad. Sci. USA* 88, 7016–7020 (1991)].

Antibodies to a native IFN-γ receptor which inhibit the binding of native IFN-γ to its receptor and thereby block IFN-γ biological activity are, for example, disclosed in EP 369,413 published May 23, 1990; EP 393,502 published Oct. 24, 1990; EP 416,652 published Mar. 13, 1991; EP 240,975 published Oct. 14, 1987; and U.S. Pat. No. 4,897,264 issued Jan. 30, 1990.

The following is a brief discussion of certain commonly used techniques that can be used for making such antibodies. Further details of these and similar techniques are found in general textbooks, such as, for example, Cabilly, et al., U.S. Pat. No. 4,816,567; Mage & Lamoyi, supra; Sambrook et al., *Molecular Cloning: A laboratory Manual*, Second Edition, Cold Spring Harbor Laboratory Press, New York, 1989; and *Current Protocols in Molecular Biology*, Ausubel et a/. eds., Green Publishing Associates and Wiley-lnterscience, 1991.

Anti-IFN-γ and anti-IFN-γ receptor antibodies acting as antagonists of IFN-γ biological action may be produced by any method known in the art. For example, the monoclonal antibodies to be used in accordance with the present invention may be made by the hybridoma method first described by Kohler & Milstein, *Nature* 256:495 (1975), or may be made by recombinant DNA methods [Cabilly, et al., supra].

In the hybridoma method, a mouse or other appropriate host animal, such as hamster is immunized with a human IFN-γ or IFN-γ receptor protein by subcutaneous, intraperitoneal, or intramuscular routes to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *J. Monoclonal Antibodies: Principles and Practice*, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse rumors available from the Salk Institute Cell Distribution Center, San Diego, Calif. USA , and SP-2 cells avaiable from the American Type Culture Collection, 10801 University Boulevard, Manassas, Va. 20110-2209. Human myeloma and mouse-human heteromyeloma cell lines also have been described for the production of human monoclonal antibodies. Kozbor, *J. Immunol.* 133:3001 (1984). Brodeur, et al., *Monoclonal Antibody Production Techniques and Applications*, pp. 51–63 (Marcel Dekker, Inc., New York, 1987)

Culture medium in which hybridoma cells are growing is assayed for production of monoclonal antibodies directed against IFN-γ or IFN-γ receptor. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The monoclonal antibodies for use in the method and compositions of the invention are those that preferentially immunoprecipitate IFN-γ or IFN-γ receptor that is present in a test sample, or that preferentially bind to IFN-γ or IFN-γ receptor in a binding assay, and are capable of blocking the detrimental effect of IFN-γ in an in vitro or in vivo model of inflammatory bowel disease.

After hybridoma cells are identified that produce antibodies of the desired specificity, affinity, and activity, the clones may be subcloned by limiting dilution procedures and grown by standard methods (Goding, J., Supra). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. Methods for purification of monoclonal antibodies are well known in the art, and are, for example disclosed in Unit 11.11 of "Current Protocols in Molecular Biology", supra, and in the references cited therein.

The amount of a specific antibody present in a hybridoma supernatant can be quantitated by either solid-phase radioimmunoassay (RIA) or by direct enzyme-linked immunoabsorbent assay (ELISA). In the solid-phase radioimmunoassay, serially diluted antiserum is incubated in microtiter wells previously coated with IFN-γ or IFN-γ receptor. Bound antibody is detected by employing $^{125}$I-labeled anti-immunoglobulin antibodies. The amount of the specific antibody in the antiserum is then determined from a standard curve generated with a specific antibody of known concentration. The unknown antiserum and the standard antibody are assayed in parallel. Protocols for the RIA procedure as used for isotype determination, and the ELISA procedure are, for example, available from Section V of "Current Protocols in Molecular Biology", supra, and from the references cited therein.

DNA encoding the monoclonal antibodies useful in the method of the invention is readily isolated and sequenced using conventional procedures (e.g., by using oligonucleotide probes that are capable of binding specifically to genes encoding the heavy and light chains of murine antibodies). The hybridoma cells described hereinabove serve as a preferred source of such DNA. Once isolated, the DNA may be placed into expression vectors, which are then transfected into host cells such as simian COS cells, Chinese Hamster ovary (CHO) cells, or myeloma cells that do not otherwise produce immunoglobulin protein, to obtain the synthesis of monoclonal antibodies in the recombinant host cells.

B. IFN-γ Variants Inhibiting the Bioloaical Activity of Native IFN-γ

The recombinant production of IFN-γ was first reported by Gray, Goeddel and co-workers [Gray et al., *Nature* 295, 503–508 (1982)], and is subject of U.S. Pat. Nos. 4,762,791, 4,929,544, 4,727,138 and 4,925,793. Recombinant IFN-γ polypeptides lacking the first three N-terminal amino acids (CysTyrCys), including variously truncated derivatives are, for example, disclosed in European Publication No. 146, 354. Non-human animal interferons, including IFN-γ, are, for example, disclosed in European Publication No. 88,622. Recombinant human gamma interferon (rhIFN-γ, Actimmune®, Genentech, South San Francisco, Calif.) received FDA approval as an immunomodulatory drug for the treatment of chronic granulomatous disease characterized by severe, recurrent infections of the skin, lymph nodes, liver, lungs, and bones due to phagocyte disfunction, and is commercially available.

Amino acid sequence, glycosylation variants and covalent derivatives of any native or recombinant IFN-γ species can be prepared by methods known in the art. Generally, particular regions or sites of the DNA encoding IFN-γ will be targeted for mutagenesis, and thus the general methodology employed to accomplish this is termed site-directed mutagenesis. The mutations are made using DNA modifying enzymes such as restriction endonucleases (which cleave DNA at particular locations), nucleases (which degrade DNA) and/or polymerases (which synthesize DNA). Restriction endonuclease digestion of DNA followed by ligation may be used to generate deletions, as described in section 15.3 of Sambrook et al., Supra.

Oligonucleotide-directed mutagenesis is the preferred method for preparing the substitution variants of IFN-γ. It may also be used to conveniently prepare the deletion and insertion variants that can be used in accordance with this invention. This technique is well known in the art as described by Adelman et al. (*DNA*, 2:183 [1983]). The oligonucleotides are readily synthesized using techniques well known in the art such, as that described by Crea et al. (*Proc. Nat'l. Acad. Sci. USA*, 75:5765 [1978]). The production of single-stranded templates for use in this technique is described in sections 4.21–4.41 of Sambrook et al., Supra.

PCR mutagenesis is also suitable for making the IFN-γ variants that can be used in the methods of the present invention. The PCR technique is, for example, disclosed in U.S. Pat. No. 4,683,195, issued Jul. 28, 1987, in section 14 of Sambrook et al., *Molecular Cloning: A Laboratory Manual*, second edition, Cold Spring Harbor Laboratory Press. New York, 1989, or in Chapter 15 of *Current Protocols in Molecular Biology*, Ausubel et al. eds., Greene Publishing Associates and Wiley-lnterscience 1991.

The DNA encoding the IFN-γ variants hereof is inserted into a replicable expression vector for further cloning and expression. Many vectors are available, and selection of the appropriate vector will depend on 1) whether it is to be used for DNA amplification (cloning) or for expression, 2) the size of the DNA to be inserted into the vector, and 3) the host cell to be transformed with the vector. Each vector contains various components depending on its function and the host cell with which it is compatible. The vector components generally include, but are not limited to, one or more of the following: a signal sequence, an origin of replication, one or more marker genes,an enhancer element, a promoter and a transcription terminator sequence.

Preferred myeloma cells are those that fuse efficienly, support stable high level expression of antibody by the selected antibody-producing cells, and are sensitive to a medium such as HAT medium. Among these, preferred myeloma cell lines are murnie myeloxia lines, such as those derived from MOPC-21 and MPC-11 mouse tumors available from the Salk Institute Cell Distribution Center, San Diego, Calif. USA, and SP-2 cells available from the American Type Culture Collection, 10801 University Boulevard, Manassas, Va. 20110–2209. Human myeloma and mouse-human heteromyeloma cell lines also have been described for the production of human monoclonal antibodies. Kozbor, *J. Immunol*. 133:3001 (1984). Brodeur, et al., *Monoclonal Antibody Production Techniques and Applications*, pp. 51–63 (Marcel Dekker, Inc., New York, 1987).

After ligation, the vector with the foreign gene inserted is transformed into a suitable host cell. The transformed cells are selected by growth on an antibiotic, commonly tetracycline (tet) or ampicillin (amp), to which they are rendered resistant due to the presence of tet and/or amp resistance genes on the vector. If the ligation mixture has been transformed into a eukaryotic host cell, transformed cells may be selected by the DHFR/MTX system described above. The transformed cells are grown in culture and the plasmid DNA (plasmid refers to the vector ligated to the foreign gene of interest) is then isolated. This plasmid DNA is then analyzed by restriction mapping and/or DNA sequencing. DNA sequencing is generally performed by either the method of Messing et al., *Nucleic Acids Res*., 9:309 (1981) or by the method of Maxam et al., *Methods of Enzymology*, 65:499 (1980).

Multicellular organisms are preferred as hosts to prepare IFN-γ variants. While both invertebrate and vertebrate cell cultures are acceptable, vertebrate cell cultures, particularly mammalian cultures, are preferable. In addition to multicellular eukaryotes, eukaryotic microbes such as filamentous fungi or yeast are suitable to prepare IFN-γ variants. *Saccharomves cerevisiae*, or common baker's yeast, is the most commonly used among lower eukaryotic host microorganisms. Prokaryotes are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include, but are not limited to, various *E. coli* strains.

Further details of the techniques and materials suitable for preparing the IFN-γ amino acid sequence variants hereof are, for example, disclosed in U.S. Pat. No. 5,108.901 issued Apr. 28, 1992, and in European Publication No. 146,354.

The glycosylation variants of native IFN-γ and its amino acid sequence variants are also prepared by techniques known in the art. Glycosylation of polypeptides is typically either N-linked or O-linked. O-linked glycoslation sites may, for example, be modified by the addition of, or substitution by, one or more serine or threonine residue to the amino acid sequence of a polypeptide. For ease, changes are usually made at the DNA level, essentially using the techniques known for the preparation of amino acid sequence variants.

Chemical or enzymatic coupling of glycosydes to IFN-γ or its amino acid sequence variants may also be used to modify or increase the number or profile of carbohydrate substituents. These procedures are advantageous in that they do not require production of the polypeptide that is capable of O-linked (or N-linked) glycosylation. Depending on the coupling mode used, the sugar(s) may be attached to (a) arginine and histidine, (b) free carboxyl groups, (c) free hydroxyl groups such as those of cysteine, (d) free sulfhydryl groups such as those of serine, threonine, or hydroxyproline, (e) aromatic residues such as those of phenylalanine, tyrosine, or tryptophan or (f) the amide group of glutamine. These methods are described in WO 87/05330 (published Sep. 11, 1987), and in Aplin and Wriston, *CRC Crit. Rev. Biochem.*, pp. 259–306 (1981).

Carbohydrate moieties present on IFN-γ or an amino acid sequence variant thereof may also be removed chemically or enzymatically. Chemical deglycosylation requires exposure to trifluoromethanesulfonic acid or an equivalent compound. This treatment results in the cleavage of most or all sugars, except the linking sugar, while leaving the polypeptide intact. Chemical deglycosylation is described by Hakimuddin et al., *Arch. Biochem. Biophys.* 259, 52 (1987) and by Edge et al., *Anal. Biochem.* 118, 131 (1981). Carbohydrate moieties can be removed by a variety of endo- and exoglycosidases as described by Thotakura et al, *Meth. Enzymol.* 138, 350 (1987). Glycosylation is suppressed by tunicamycin as described by Duskin et al., *J. Biol. Chem.* 257,3105 (1982). Tunicamycin blocks the formation of protein-N-glycosydase linkages.

Glycosylation variants can also be produced by selecting appropriate host cells. Yeast, for example, introduce glycosylation which varies significantly from that of mammalian systems. Similarly, mammalian cells having a different species (e.g. hamster, murine, insect, porcine, bovine or ovine) or tissue (e.g. lung, liver, lymphoid, mesenchymal or epidermal) origin than the source of the selectin variant, are routinely screened for the ability to introduce variant glycosylation.

The use of covalent derivatives of IFN-γ amino acid sequence and glycosylation variants is within the scope hereof. Such modifications are introduced by reacting targeted amino acid residues of the IFN-γ variant with an organic derivatizing agent that is capable of reacting with selected side chains or terminal residues, or by harnessing mechanisms of post-translational modification that function in selected recombinant host cells. Covalent derivatization may be instrumental in turning biologically active IFN-γ variants to derivatives which retain the qualitative ability of the corresponding native IFN-γ to bind its receptor but are devoid of biological activity, or improve other properties, i.e. half-life, stability, etc. of the molecule. Such modifications are within the ordinary skill in the art and are performed without undue experimentation. Certain post-translational derivatization are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues fall within the scope of the invention. Other post-translational modifications include hydroxylation of proline and lysine, phosphorylation of hydroxyl groups of seryl and threonyl residues, methylation of the α-amino groups of lysine, arginine, and histidine side chains [T. E. Creighton, *Proteins: Structure and Molecular Properties*, W. H. Freeman Co., San Francisco pp. 79–86 (1983)], acetylation of the N-terminal amines and, in some instances, amidation of the C-terminal carboxyl of IFN-γ. Other covalent derivatives comprise IFN-γ covalently bonded to a nonproteinaceous polymer, such as polyethylene glycol, polypropylene glycol or polyoxyalkylenes, in the manner set forth in U.S. Pat. Nos. 4,640,835; 4,496,689; 4,301,144; 4,670,417; 4,791,192, 4,179,337, or 5,116,964.

A specific group of IFN-γ variants includes the fusion of a contiguous IFN-γ amino acid sequence antagonizing the biological action of native IFN-γ to a stable plasma protein, such as an immunoglobulin. The structure and construction of such fusion proteins (such as immunoadhesins) will be detailed hereinbelow with reference to IFN-γ receptors. IFN-γ-stable plasma protein fusions are made in an analogous manner.

Receptor binding domains in IFNs-γ from various species, such as human and mouse, have been identified [see, for example, Lord, S. C. et al., *Mol. Immunol*. 26,637–640 (1989); Favre, C. et al., *Mol. Immunol*. 26, 17–25 (1989); Jarpe, M. A. and Howard, M. J., *J. Immunol*. 145, 3304–3309 (1990); Magazine, H. I. and Johnson, H. M., *Biochemistry* 30, 5784–5789 (1991)].

C. IFN-γ Receptor

IFN-γ receptors purified from native source or produced by techniques of recombinant DNA technology are known in the art, and are, for example disclosed in the following publications: Aguet, M. & Merlin, G., *J. EXD. Med*. 165, 988–999 (1987); Novick, D. et al., *J. Biol. Chem*. 262, 8483–8487 (1987); Calderon, J. et al.,*Proc. Natl. Acad. Sci. USA* 85, 4837–4841 (1988); Basu, M. et al., *Proc. Natl. Acad. Sci. USA* 85, 6282–6286 (1988); Aguet et al., *Cell* 55,273–280 (1988); Gray, P. W. et al., *Proc. Natl. Acad. Sci. USA* 86, 8497–8501 (1989).

Amino acid sequence and glycosylation variants and covalent modifications of a native (human or non-human) IFN-γ receptor can be made following the same general techniques described hereinabove for IFN-γ.

An IFN-γ receptor amino acid sequence capable of binding native IFN-γ can also be linked to a stable plasma protein sequence as hereinbefore defined. The stable plasma protein sequence may, for example, be an immunoglobulin sequence, preferably an immunoglobulin constant domain sequence. The resultant molecules are commonly referred to as IFN-γ receptor-immunoglobulin chimeras or, more recently, immunoadhesins.

Ordinarily, the C-terminus of a contiguous amino acid sequence of a ligand- (IFN-γ-) binding domain of an IFN-γ receptor is fused to the N-terminus of a contiguous amino acid sequence of an immunoglobulin constant region, in place of the variable region(s), however N-terminal fusions are also possible.

Typically, such fusions retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, immunoadhesins may be synthesized according to known methods.

The precise site at which the fusion is made is not critical; particular sites are well known and may be selected in order to optimize the biological activity, secretion or binding characteristics of the immunoadhesins.

In a preferred embodiment, the C-terminus of a contiguous amino acid sequence which comprises the binding site(s) for IFN-γ is fused, at the N-terminal end, to the C-terminal portion of an antibody (in particular the Fc domain), containing the effector functions of an immunoglobulin, e.g. immunoglobulin $G_1$ (IgG-1). As hereinabove mentioned, it is possible to fuse the entire heavy chain constant region to the sequence containing the binding site(s). However, more preferably, a sequence beginning in the hinge region just upstream of the papain cleavage site (which defines IgG Fc chemically; residue 216, taking the first residue of heavy chain constant region to be 114 [Kobet et al., supra], or analogous sites of other immunoglobulins)

is used in the fusion. Although it was earlier thought that in immunoadhesins the immunoglobulin light chain would be required for efficient secretion of the heterologous protein-heavy chain fusion proteins, it has been found that even the immunoadhesins containing the whole IgG1 heavy chain are efficiently secreted in the absence of light chain. Since the light chain is unnecessary, the immunoglobulin heavy chain constant domain sequence used in the construction of the immunoadhesins of the present invention may be devoid of a light chain binding site. This can be achieved by removing or sufficiently altering immunoglobulin heavy chain sequence elements to which the light chain is ordinarily linked so that such binding is no longer possible. Thus, the CH1 domain can be entirely removed in certain embodiments of the IFN-γ receptor-immunoglobulin chimeras.

In a particularly preferred embodiment, the amino acid sequence containing the extracellular domain of an IFN-γ receptor is fused to the hinge region and CH2, CH3; or CH1, hinge, CH2 and CH3 domains of an IgG-1, IgG-2, IgG-3, or IgG-4 heavy chain. The construction of a typical structure is disclosed in Example 1.

In some embodiments, the IFN-γ receptor-immunoglobulin molecules (immunoadhesins) are assembled as monomers, dimers or multimers, and particularly as dimers or tetramers. Generally, these assembled immunoadhesins will have known unit structures similar to those of the corresponding immunoglobulins. A basic four chain structural unit (a dimer of two immunoglobulin heavy chain-light chain pairs) is the form in which IgG, IgA and IgE exist. A four chain unit is repeated in the high molecular weight immunoglobulins; IgM generally exists as a pentamer of basic four-chain units held together by disulfide bonds. IgA globulin, and occasionally IgG globulin, may also exist in a multimeric form in serum. In the case of multimers, each four chain unit may be the same or different.

It is not necessary that the entire immunoglobulin portion of the IFN-γ receptor-immunoglobulin chimeras be from the same immunoglobulin. Various portions of different immunoglobulins may be combined, and variants and derivatives of native immunoglobulins can be made as hereinabove described with respect to IFN-γ, in order to optimize the properties of the immunoadhesin molecules. For example, immunoadhesin constructs in which the hinge of IgG-1 was replaced with that of IgG-3 were found to be functional and showed pharmacokinetics comparable to those of immunoadhesins comprising the entire IgG-1 heavy chain.

The IFN-γ receptor-immunoglobulin immunoadhesins may contain two different binding domains not ordinarily present in an immunoglobulin molecule. In a specific embodiment, the two binding domains are two different IFN-γ binding amino acid sequences from an IFN-γ receptor. In another embodiment, only one binding domain is from an IFN-γ receptor, whereas the other is a different polypeptide sequence not ordinarily present in an immunoglobulin molecule. The second binding domain preferably is an amino acid sequence capable of binding a polypeptide implicated in the initiation or development of IBD. This second binding sequence preferably is from a second IFN-γ inhibitor, an IL-1 inhibitor, a TNF-α inhibitor, a CD11a/18 inhibitor, a CD11b/18 inhibitor, or an L-selectin inhibitor, and may comprise the antibody-antigen combining site of an antibody to IFN-γ, IL-1, TNF-α, CD11a/18, CD11b/18, L-selectin, or to the respective receptors/ligands, or may, for example, be an IL-1 receptor or type 1 or type 2 TNF-α receptor (TNF-R1 or TNF-R2) amino acid sequence. If both binding domains in a chimeric immunoglobulin molecule are from antibodies of different binding specificities, the structure is commonly referred to as bispecific antibody.

Diagrams illustrating the possible structures of mono- and bispecific immunoadhesins are, for example, disclosed in U.S. Pat. No. 5,116,964 issued May 26, 1992, as are chains or basic units of varying structure which may be utilized to assemble the monomers and hetero- and homo-multimers of immunoglobulins in such constructs.

Bispecific immunoadhesins and antibodies are also disclosed in EP 355,068 published Feb. 21, 1990, and PCT application publication no. WO 91/05871 published May 2, 1991.

In certain cases it may be advantageous to prepare trimeric bispecific immunoadhesins, where in one arm of a Y-shaped immunoglobulin, the first heavy chain constant domain (CH1) is removed or altered to eliminate its ability to covalently bind to an immunoglobulin light chain (i.e. the light chain binding site is eliminated or inactivated), while in the other arm the light chain binding site within the CH1 domain is retained, and is covalently linked to an immunoglobulin light chain. In each arm, the heavy chain constant domain sequences are fused to "binding domains" (replacing the heavy chain variable domains) which are different from one another. One of the binding domains is from an IFN-γ antagonist, whereas the other binding domain may be selected from the cytokine antagonists referred to hereinabove. The resultant structure is a trimer with two different binding specificities (heterotrimer) composed of an immunoglobulin heavy chain constant domain sequence fused to a first binding domain and a second immunoglobulin heavy chain constant domain sequence fused to a different binding domain and covalently linked to an immunoglobulin light chain.

Two or more of the heterotrimers may be covalently linked to each other to provide a multimeric structure. Generally, these assembled bispecific immunoadhesins will have known unit structures. A three-chain unit may be repeated similarly to the higher molecular weight immunoglobulins.

In another embodiment, fusion proteins with two specificities may be made by fusing the IFN-γ receptor amino acid sequence to the 3' end of an antibody heavy chain, where the antibody may, for example, be an anti-IFN-γ antibody, or any of the other antibodies referred to hereinabove. The IFN-γ receptor amino acid sequence may, for example, be inserted wither between the hinge and CH2 domains, or between the CH2 and CH3 domains of the immunoglobulin heavy chain. The chimeric immunoglobulin heavy chain-IFN-γ receptor gene may then be introduced into an immunoglobulin light chain secreting transfectoma cell line, producing the light chain of the desired antibody. The construction of similar structures was reported by Hoogenboom, H. R., *Mol. Immunol.* 28, 1027–1037 (1991).

Linear fusion proteins with dual specificity, comprising the fusion of an IFN-γ receptor amino acid sequence to an antibody sequence may be prepared essentially as described by Traunecker et al., *EMBO* 10, 3655–3659 (1991).

Traunecker et al. designed a single-chain polypeptide, containing the FvCD3, the two N-terminal domains of CD4 and C-kappa, designated Janusin (CD4-FvCD3-Ckappa). This bispecific linear molecule was purified by using anti-kappa affinity columns. Linear molecules comprising an IFN-γ receptor amino acid sequence can be made in an analogous manner.

Immunoglobulins and certain variants thereof are known and many have been prepared in recombinant cell culture. For example, see U.S. Pat. No. 4,745,055; EP 256,654; Faulkner et al., *Nature* 298:286 (1982); EP 120,694; EP 125,023; Morrison, *J. Immun.* 123:793 (1979); Köhler et al.,

*Proc. Nat'l. Acad. Sci. USA* 77:2197 (1980); Raso et al., *Cancer Res.* 41:2073 (1981); Morrison et al., *Ann. Rev. Immunol.* 2:239 (1984); Morrison, *Science* 229:1202 (1985); Morrison et al., *Proc. Nat'l. Acad. Sci. USA* 81:6851 (1984); EP 255,694; EP 266,663; and WO 88/03559. Reassorted immunoglobulin chains also are known (see for example U.S. Pat. No. 4,444,878; WO 88/03565; and EP 68,763 and references cited therein), as are synthetic antibody binding sites (Fv analogues) produced by protein engineering [see e.g. Huston, J. S. et al., *Proc. Natl. Acad. Sci. USA* 85, 5879–5883 (1988), and U.S. Pat. No. 5,091,513 issued Feb. 25, 1992].

The selection of the immunoglobulin that provides the (heavy chain) constant domain sequences in the IFN-γ receptor immunoglobulin immunoadhesins of the present invention, is a matter of choice, largely depending on the motivation for constructing them. If the extension of plasma half-life of the IFN-γ receptor is a consideration, immunoglobulins of IgG-1, IgG-2 and IgG-4 isotypes are good candidates, as they all have in vivo half-lives of 21 days, as opposed to IgG-3 which has an in vivo half-life of 7 days. Further differences that might be advantages or detriments in certain situations are, for example, in complement activation. IgG-1, IgG-2 and IgG-3 all activate complement, however, IgG-2 is significantly weaker at complement activation than IgG-1 and does not bind to Fc receptors on mononuclear cells or neutrophils, while IgG-3 shows better complement activation than IgG-1. IgG-1 has only four serologically-defined allotypic sites, two of which (G1 ml and 2) are in the Fc portion; for two of these sites (G1m1 and 17) one allotype is non-immunogenic. In contrast, there are 12 serologically defined allotypes in IgG-3, all of which are in the Fc portion, only three of which (G3m5, 11 and 21) have an allotype which is non-immunogenic. Thus, for repeated and long-term therapeutic applications, immunoadhesins with IgG-1 derived constant domain sequences are preferred. It is possible to use immunoglobulins from different classes or isotypes in the two arms of the bispecific immunoadhesin molecule. It is further possible to combine sequences from various immunoglobulin classes or isotypes in the same arm of a bispecific molecule, or in both arms of a mono- or bispecific immunoadhesin.

The IFN-γ receptor-immunoglobulin chimeras may be prepared by standard techniques of recombinant DNA technology detailed hereinabove. Another alternative is to chemically synthesize the gene encoding the chimeras using one of the methods described in Engels et al., *Agnew. Chem. Int. Ed. Engl*. 28, 716 (1989). These methods include triester, phosphite, phosphoramidite and H-phosphonate methods, PCR and other autoprimer methods, and oligonucleotide syntheses on solid supports.

Fusion proteins comprising other stable plasma proteins can be made by methods known in the art. For example, fusion proteins comprising N-terminal fragments of human serum albumin (HSA) as stable plasma protein are disclosed in EP 399,666 published Nov. 28, 1990.

D. Selection of IFN-γ Inhibitors

The IFN-γ inhibitor useful in performing the method of the present invention may be tested by a number of in vitro and in vivo methods.

Binding Assays

The ability of an inhibitor to bind IFN-γ (such as in the case of IFN-γ receptor or anti-IFN-γ antibodies) can, for example, be tested by equilibrium binding analysis, essentially as described by Ashkenazi, A. et al., *Proc. Natl. Acad. Sci. USA* 88, 10535–10539 (1991). According to this method, the IFN-γ inhibitor candidate is immobilized onto microtiter wells coated with goat anti-human IgG Fc antibody, and is incubated with detectably labeled IFN-γ. A similar method is described in Examples 5B and 5C of EP 393,502 published Oct. 24, 1990. Alternatively or in addition, the affinity of binding can be tested in competition binding assays, such as, for example, disclosed by Fountoulakis, M. et al., *J. Biol. Chem*. 265, 13268–13275 (1990). The ability of an IFN-γ inhibitor as defined for the purpose of the present invention, to inhibit IFN-γ binding to its receptor (e.g. IFN-γ variants and anti-IFN-γ receptor antibodies) can be tested in an analogous manner. If the label is radioactive, the binding can be quantitated by a γ or β scintillation counter.

IFN-γ Biological Activity Assays

The ability of IFN-γ inhibitors to block the biological activity of IFN-γ can be tested in any conventional in vitro assays of IFN-γ action. For example, the ability of an inhibitor to block the induction of expression of specific antigens by IFN-γ can be assayed, essentially as described in Example 2. In another group of assays (antiviral assays), the ability of an inhibitor candidate to block the protective effect of IFN-γ against viral infection is tested. A specific antiviral assay is disclosed in Example 2. Alternatively or in addition, one can use a host immune-response model to test the ability of an IFN-γ inhibitor to block endogenous IFN-γ, for example as disclosed in Example 2 hereinafter. The same example also discloses a suitable mouse model for testing IFN-γ inhibitor action.

In vitro Model of IBD

An in vitro model of IBD has been developed by MacDonald, T. and co-workers, and in described by Braegger, C. P. and MacDonald, T. in Chapter 8 of "Immunology of Gastrointestinal Disease", supra, and has earlier been reported by MacDonald, T. and Spencer, J., *J. Exp. Med*. 167, 1341–1349 (1988). In this model, small explants (1–2 mm across) of human fetal gut tissue (small or large bowel) containing T lymphocytes at the stage of 15–20 weeks gestation are cultured. The human fetal gut can be maintained in organ culture for several weeks with retention of morphology, epithelial cell renewal and enterocyte function. All of the T cells in the explant can be activated by culturing in the presence of pokeweed mitogen or monoclonal anti-CD3 antibodies. The gross appearance of the explants shows major changes as a result of T cell activation. The changes in the small bowel explants as a result of T cell activation are reminiscent of the mucosal change seen in early stages of Crohn's disease, and the goblet cell depletion seen in colon explants is also a feature of ulcerative colitis. This model can be used to study the interaction of T cells with the gut epithelium and specifically, to observe responses to T cell activation, such as secretion of IFN-γ, and blocking of IFN-γ secretion by giving an IFN-γ inhibitor candidate prior to or at the time of T cell activation.

Animal Models of IBD

The first group of animal models of IBD includes animals spontaneously developing diseases reminiscent of some forms of IBD. Spontaneous animal models include C3H/HeJ mouse, Japanese waltzing mice, swine dysentery and equine colitis, caused by *C. difficile*, and the cotton top tamarin. The diseases that these animals suffer have recently been subdivided into five types, two of which resemble UC. Of these models, tamarin are preferred, as a large proportion of these animals have some form of gut disorder, and many of them also develop bowel cancer, as do patients with UC.

In another approach, various irritants, such as ethanol, acetic acid, formalin, immune complexes, trinitrobenzene sulphonic acid (TNBS), bacterial products or carrageenan are used to generate acute or chronic inflammation. A model of this kind has been developed by Wallace, J. and coworkers [Morris et al. *Gastroenterology* 96, 795 (1989)].

According to a third approach, transgenic animals are used to model IBD. Most human patients who have ankylosing spondylitis also carry the gene for HLA-B27. It has been observed that such patients are at greater risk of developing IBD. HLA-B27 transgenic rats, which were attempted to model spondyloarthropathies, in addition to the joint disease, also showed symptoms of chronic inflammation of the bowel which, though not identical, had many similarities with CD. Accordingly, the HL-B27 transgenic rats can be used to model IBD.

Another suitable transgenic animal model is based on IL-10 "knockout" mice. IL-10 is produced by TH2 cells, stimulates B cells to produce antibody, downregulates macrophages reducing the production of IL-1, IL-6, IL-8 and TNF-α, and shifts the balance of antigen presentation from macrophages to B cells. IL-10 also reduces the production of IFN-γ, hence reducing the activity of TH1 cells and natural killer cells. Mice treated from birth with anti-IL-10 antibody (given i.p. 3-times weekly) show no changes in body weight or histology of major tissues. The number and proportions of B and T cell lymphocytes are also normal. There is, however, a dramatic reduction in IgA production, whereas the concentrations of IgG-2a and IgG-2b are increased. In addition, an almost total depletion of peritoneal B cells, which are a special B cell population carrying the marker Ly-1, was observed. These B cells are continuously derived from bone marrow, have a limited immunoglobulin repertoire which is not subject to somatic mutation, and are responsible for much of the IgM found in plasma. The depletion of these specific B cells may be due to the increased level of IFN-γ that are produced in the anti-IL-10 antibody-treated mice. This is supported by the observation that if IFN-γ is given at the same time as the anti-IL-10 antibody, the Ly-1 B cells survive.

Usually the screening for antagonists suitable for the purpose of the present invention includes a combination of the foregoing assays, the results obtained in vitro and in vivo models of IBD being the most conclusive.

E. Pharmaceutical Compositions

The IFN-γ inhibitors of the present invention, including the bispecific molecules herein, are usually administered as pharmaceutical compositions, usually formulated in dosage forms by methods known in the art; for example, see Remington's Pharmaceutical Sciences, Mack Publishing Company, Easton, Pa., 15th Edition 1975. For parenteral administration, the antagonists are typically formulated in the form of injectable solutions, suspensions or emulsions, in admixture with a suitable pharmaceutically acceptable vehicle and optionally other pharmaceutically acceptable additives. Typical vehicles include saline, dextrose solution, Ringer's solution, etc., but non-α queous vehicles may also be used.

Pharmaceutical compositions comprising IFN-γ receptor amino acid sequences and antagonist anti-IFN-γ receptor antibodies along with suitable dosages and dose rates are, for example, disclosed in EP 369,413 published May 23, 1990; EP 393,502 published Oct. 24, 1990; EP 416,652 published Mar. 13, 1991; EP 240,975 published Oct. 14, 1987; and U.S. Pat. No. 4,897,264 issued Jan. 30, 1990.

The formulation of IFN-γ variants is preferably liquid, and is ordinarily a physiological salt solution or dextrose solution, together with conventional stabilizers and/or excipients. IFN-γ compositions may also be provided as lyophilized powders. IFN-γ-containing pharmaceutical compositions are, for example, disclosed in U.S. Pat. No. 4,727,138 issued Feb. 23, 1988, U.S. Pat. No. 4,762,791 issued Aug. 8, 1988, U.S. Pat. No. 4,925,793 issued May 15, 1990, U.S. Pat. No. 4,929,553 issued May 29, 1990, U.S. Pat. No. 4,855,238 issued Aug. 8, 1989. A typical formulation may contain IFN-γ ($20 \times 10^6$ U) at 1.0 or 0.2 mg/ml, 0.27 mg/ml succinic acid, and disodium succinate hexahydrate 0.73 ml/injection at pH 5.0. Preferred IFN-γ formulations and dose ranges are disclosed in U.S. Pat. No. 5,151,265 issued Sep. 29, 1992. The formulations and dosages for anti-IFN-γ receptor antibodies are similar, and can be determined without undue experimentation.

The actual dose for each particular IFN-γ inhibitor will depend on the medical condition to be treated, the pathological condition and clinical tolerance of the patient involved, the properties of the preparations employed, including their activity and biological half-life, etc. It will be appreciated that the practitioner will adjust the dose in line with clinical experience.

The inhibitors of the present invention many be applied prophylactically to patients known to be at risk of developing a disease to be treated or subsequent to the onset of the disease. Such patients are, for example, those diagnosed with and possibly treated for inflammatory bowel disease on at least one earlier occasion but asymptomatic at the time of administration.

The IFN-γ inhibitors of the present invention may be administered in combination with other therapeutics potentially useful in the treatment of a condition characterized by a decrease in the IgA/IgG ratio, such as inflammatory bowel disease. These other therapeutics may be antiinflammatory agents, such as sulfasalazine, corticosteroids, 6-mercaptopurine/azathioprine; immunosuppressants such as cyclosporine, prostaglandin inhibitors; superoxide dismutase; IL-1 receptor antagonists; anti-ELAM-1 (E-selectin) antibodies; inhibitors of VCAM-1 binding to eosinophils; anti-CD18 antibodies. The administration may be simultaneous or consecutive, and includes the administration of formulations comprising one or more of these and similar therapeutics in combination with one or more IFN-γ inhibitor. Alternatively, such further therapeutics may be included in the fusion polypeptides (bispecific immunoadhesins, antibodies, linear molecules) of the present invention.

Further details of the invention are set forth in the following non-limiting examples.

EXAMPLE 1

Construction of Human and Murine IFN-γ Receptor-immunoadhesins

IFN-γ receptor (IFNγR) immunoadhesins were constructed from plasmids pRK-HγR or pRK-MγR [Gibbs, V. C. et al., *Mol. Cell. Biol.* 11, 5860–5866. (1991)], encoding the human and murine IFNγR, respectively, and plasmid pRKCD4$_2$Fc$_1$, encoding CD4-IgG-1 [Byrn, R. A. et al., *Nature* 344, 667–670 (1990)]. Briefly, this CD4-IgG-1 construct consists of residues 1–180 of the mature human CD4 protein fused to human IgG-1 sequences beginning at aspartic acid 216 (taking amino acid 114 as the first residue of the heavy chain constant region [Kabat et al., supra]) which is the first residue of the IgG-1 hinge after the cysteine residue involved in heavy-light chain bonding, and ending with residue 441. This molecule contains the CD4 V1 and V2 domains, linked to the hinge and Fc (CH2 and CH3) domains of human IgG-1, and is designated CD4$_2$Fc1.

Complementary DNA (cDNA) fragments encoding the human or murine IFNγR (each with its natural sign sequence) were generated by digestion of the respective plasmids with Cla I and Hind III. Plasmid pRKCD4₂Fc₁ was digested with Cla I and Nhe I to remove most of the CD4 sequence while retaining the human IgG-1 heavy chain hinge region and CH2 and CH3 domain sequences. Intermediate plasmids were constructed by inserting each IFNγR sequence 5' of the IgG-1 sequence and in the same reading orientation, by ligating the respective Cia I sites and by blunting and ligating the Hind III and Nhe I sites. Next, the remaining CD4 sequence and the sequence encoding the transmembrane and intracellular portion of each IFNγR were removed by oligonucleotide-directed deletion mutagenesis to create the exact junction between the extracellular portion of each IFNγR and the IgG-1 hinge. At the junctions are the codons for glycine-231 or aspartic acid-216 of the human or murine IFNγR and the additional 226 codons of human IgG-1 heavy chain. Thus, the mature hIFNγR-IgG-1 and mIFNγR-IgG-1 polypeptides are 448 and 44 amino acids long, respectively. Deletion mutagenesis was done using synthetic oligonucleotides complementary to the 18 bases on each side of the desired junctions as primers, and the above intermediate plasmids as templates, as described by Ashkenazi, A. et al., *Proc. Natl. Acad. Sci. USA* 88, 10535–10539 (1991). The final structure was confirmed by DNA sequencing.

The IFNγR-IgG-1 immunoadhesins (also referred to as IFNγR-IgG) were expressed in human embryonic kidney (HEK) 293 cells by transient transfection using a modification of the calcium phosphate precipitation method [Marsters, S. A. et al, *J. Biol. Chem.* 267, 5747–5750 (1992)]. The immunoadhesins were purified from serum-free cell culture supernatants in a single step by affinity chromatography on Stapylococcus aureus Protein A taking advantage of the binding of the IgG-1 Fc domain to Protein A. Bound proteins were eluted with 50 mM sodium citrate pH 3/20% (w/v) glycerol and the eluted pools were neutralized with 0.05 volumes of 3M Tris HCl pH 8 to 9. IFNγR-IgG-1 processed in this way was more than 95% pure. The obtained constructs comprise the fusion of the extracellular portion of human (h) or murine (m) IFNγR with the hinge region and CH2 and CH3 domains of IgG-1 heavy chain (FIG. 1A)

We examined the subunit structure of the immunoadhesins by polyacrylamide gel electrophoresis (FIG. 1 B–D). Under non-reducing conditions, a predominant band with a relative molecular mass (Mr) of 160–220 kDa was observed for both human and murine IFNγR-IgG-1; under reducing conditions, this band was absent and a new band of 65–90 kDa appeared (FIG. 1B). This indicates that each IFNγR-IgG-1 is secreted as a disulfide-bonded homodimer. The broad range of Mr probably is due to substantial glycosylation of the immunoadhesins, as there are five potential N-linked glycosylation sites in the IFNVR region [Aguet, M. et al, *Cell* 55, 273–280 (1988); Cofano, F. et al., *J. Biol. Chem.* 265,4064–4071 (1990); Gray, R. W. et al., *Proc. Natl. Acad. Sci. USA* 86, 8497–8501 (1989); Hemmi, S. et al., *Proc. Natl. Acad. Sci. USA* 86, 9901–9905 (1989); Kumar, C. S. et al., *J. Biol. Chem.* 264, 17939–17946 (1989); Munro, S. and Maniatis, T., *Proc. Natl. Acad. Sci. USA* 86, 9248–9252 (1989)] and one in the IgG-1 region [Byrn, R. A., 1990, supra]. Western blots using polyclonal anti-IgG Fc antibodies confirmed the identity of the 160–220 kDa band as IFNγR-IgG-1; immunoreactivity with the anti-IgG antibodies was diminished upon reduction, probably due to disruption of the disulfide-stabilized domain structure of the Fc portion (FIG. 1C). Ligand blots with [$^{125}$I]-labeled human or murine IFN-γ revealed the same Mr band, which was not labeled in the presence of excess cold IFN-γ from the respective species (FIG. 1D). These results demonstrate the presence of an IgG-1 heavy chain and of a functional receptor domain that binds IFN-γ specifically in both IFNγR-IgG-1 molecules. The human and murine IFN-γ receptors are about 50% identical at the amino acid level, and both bind IFN-γ in a species-specific manner (Finbloom, D. S. et al., *J. Immunol.* 135, 300–305 (1985); Ucer, U. et al., *Int. J. Cancer.* 36, 103–108 (1991)].

EXAMPLE 2

Testing of IFN-γ Inhibitor Activity

1. Assays

IFNv binding assays. The binding of IFNγR-IgGs to IFN-γ was analyzed essentially as described [Ashkenazi et al., *Proc. Natl. Acad. Sci. USA* 88: 10535–10539 (1991)]. Each IFNγR-IgG (1 μg/ml) was immobilized onto microtiter wells coated with goat anti-human IgG Fc antibody. Human or murine IFNγR-IgG was incubated with recombinant, [$^{125}$I]-labeled human (h) or murine (m) IFN-γ (radioiodinated using lactoperoxidase to a specific activity of 20–30 μCi/μg) in phosphate buffered saline (PBS) containing 1% bovine serum albumin (BSA) for 1 h at 24° C. Nonspecific binding was determined by omitting IFNγR-IgGs.

IFN-γ induction of gene expression assays. The biological activity of IFNγR-IgG in vitro was assessed by testing its ability to block the induction of expression of specific antigens by IFN-γ. Human HeLa cells or mouse L929 cells were grown to 30% confluency and incubated for 48 hr at 37° C./5% $CO_2$ with 10 ng/ml of hIFN-γ or mIFN-γ, respectively. IFNγR-IgG from the respective species, or CD4-IgG as a negative control, also was added to the cultures. The expression of ICAM-1 by the human cells and of the class I MHC antigen H-2K$^k$ by the murine cells was then analyzed by flow cytometry, using specific fluoresceinated antibodies. Propidium iodide was added immediately before analysis to gate out nonviable cells.

IFNγ antiviral activity assays. The ability of IFNγR-IgG to block the protective effect of IFN-γ against infection of cells with encephalomyocarditis virus (EMCV) also was tested as a measure of the immunoadhesin's inhibitory activity in vitro. We used a modification of a method described previously [Rubinstein et al.,*J. Virol.* 37: 755–758 (1981)]. Human A549 or murine L929 cells were plated in microtiter dishes (2 x 104 cells/well) and incubated at 37° C./5% $CO_2$ for 24 hr. Then, recombinant human or murine IFN-γ was added at concentrations of 0.125 or 0.5 ng/ml, respectively, concomitant with human or murine IFNγR-IgG, and the incubation was continued for 24 h. EMCV was then added to the cells at 1 multiplicity of infection unit per well. The survival of the cells was quantitated by crystal violet exclusion 18–24 hr later.

Murine listeriosis. The ability of IFNγR-IgG to block endogenous IFN-γ in vivo was investigated in a host immune-response model, using Listeria monocytogenes infection in mice [Buchmier and Schreiber, *Proc. Natl. Acad. Sci USA* 82: 7404–7408 (1985); Farber and Peterkin, *Microbiological Reviews* 55: 476–511 (1991)]. Female C57BL/6xDBA/2F. (BDF1) mice, stated to be free of infection by adventitious viral agents, were obtained at 6 weeks of age from Charles River (Portage, Mich.). The L. monocytogenes was maintained as described previously [Haak-Frendscho, et al., *Infect. Immun.* 57: 3014–3021 (1989)]. Log-phase bacteria were suspended in tryptone phosphate broth containing 20% glycerol and stored as aliquots at −70° C. Mice were given an intraperitoneal (i.p.) injection of vehicle, CD4-IgG as a negative control, or mIFNγR-IgG. Immediately after, each mouse received 4×10⁴ freshly thawed bacteria in 0.2 ml pyrogen-free PBS by intravenous (i.v.) injection via a lateral tail vein. Three days later, the mice were euthanized and their spleens and livers were removed and homogenized in separate sterile tissue grinders containing 1 ml sterile water. The homogenates were diluted serially and plated onto agar. Plates were incubated 24 hr at 37° C., whereafter the bacterial colonies were enumerated. Mouse model for contact-sensitivity. The ability of IFNγR-IgG to block endogenous IFN-γ in vivo was investigated further using a mouse model for contact-sensitivity. Balbic mice (Charles River, Portage, Mich.) were anesthetized by i.p. injection of Ketamine/Xylazene. A 3×3 cm square patch on the abdomen was shaved, where 200 µg of 2,4-dinitro-1-fluorobenzene (DNFB) was applied topically (sensitization). Five days later, 20 µg of DNFB was applied topically to both sides of the left pinna, whereas diluent was applied to both sides of the right pinna (challenge). Ten hours later, the mice were injected i.v. via a lateral tail vein with 2 µCi of [$^{125}$I]UdR. Sixteen hours later, the mice were euthanized, the pinnae were removed at the hairline, and [12511 radioactivity was counted as a measure of lymphocyte proliferation and migration to the pinnae. Mice treated with IgG, immunoadhesins, or monoclonal antibodies were injected i.v. with vehicle or agent 30 min prior to sensitization and 30 min prior to challenge.

2. Results

Binding of IFNγR-IqG to IFN-γ. We investigated the binding of the human and murine immunoadhesins to IFN-γ by equilibrium binding analysis (FIG. 2). Each IFNγR-IgG exhibited specific and saturable binding to [$^{125}$I-labeled IFN-γ from the autologous species. Scatchard analysis indicated dissociation constant ($K_d$) values of 1.5 nM for hIFNγR-IgG with 1$^{125}$I]hIFN-γ and 3.3 nM for mIFNγR-IgG with [$^{125}$I]mIFN-γ. Competition binding assays (data not shown) showed no significant inhibition by mIFN-γ of hIFN-γ binding to hIFNγR-IgG, or by hIFN-γ of mIFN-γ binding to mIFNγR-IgG. These results indicate that each immunoadhesin binds IFN-γ in a species-specific manner, consistent with previous reports [Finbloom et al., J. Immunol. 135: 300–305 (1985); Ucer, et al, Int. J. Cancer 36: 103–108 (1985)]. The IFN-γ binding affinity of IFNγR-IgG is comparable to that reported for recombinant soluble IFNγR [Fountoulakis, et al, J. Biol. Chem. 265: 13268–13275 (1990)]. Therefore, the attachment of the IFNγR extracellular domain to the IgG heavy-chain does not hinder IFN-γ binding.

Figure 3B:
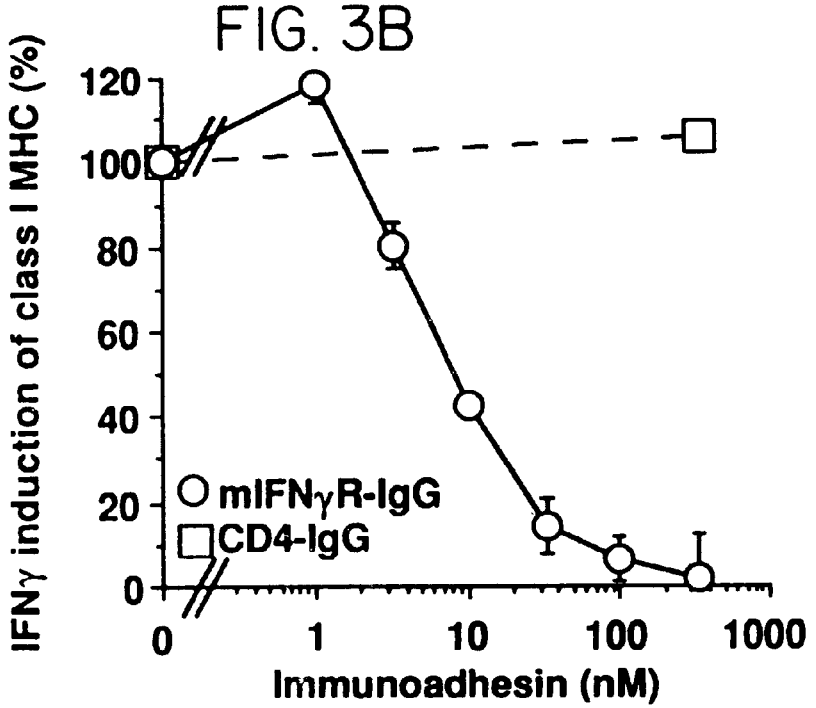

IFNγR-laG blocks IFNγ in vitro. We tested the ability of human and murine IFNγR-IgG to inhibit immunomodulatory and antiviral effects of IFN-γ on cultured cells (FIG. 3). The induction of ICAM-1 by hIFN-γ in human HeLa cells could be blocked completely by hIFNγR-IgG, with half-maximal inhibition (IC$_{50}$) at about 13 nM of immunoadhesin. In contrast, CD4-IgG, used as a negative control, had no effect (FIG. 3A). Similarly, the induction of class I MHC antigen H-2K$^k$ by mIFN-γ in mouse L929 cells could be blocked completely by mIFNγR-IgG, with an IC$_{50}$ of about 10 nM, whereas CD4-IgG had no effect (FIG. 3B). The cytopathic effect of encephalomyocarditis virus (EMCV) can be prevented by addition of IFN-γ. In EMCV-infected human A549 cells, hIFNγR-IgG blocked the antiviral effect of hIFN-γ completely, with an IC$_{50}$ of about 8 nM (FIG. 3C). Similarly, mIFNγR-IgG blocked the antiviral effect of mIFN-γ in EMCV-infected mouse L929 cells, with an IC$_{50}$ of about 10 nM (FIG. 3D). In all experiments performed, IFNγR-IgG from the alternate species had no significant effect on antiviral activity, confirming the species selectivity of the interaction between the immunoadhesins and IFN-γ. These results demonstrate the ability of IFNγR-IgG to block efficiently and completely the interaction of IFN-γ with its cell-surface receptor, thus preventing the cytokine from exerting biological effects on cells in vitro.

Figure 4:
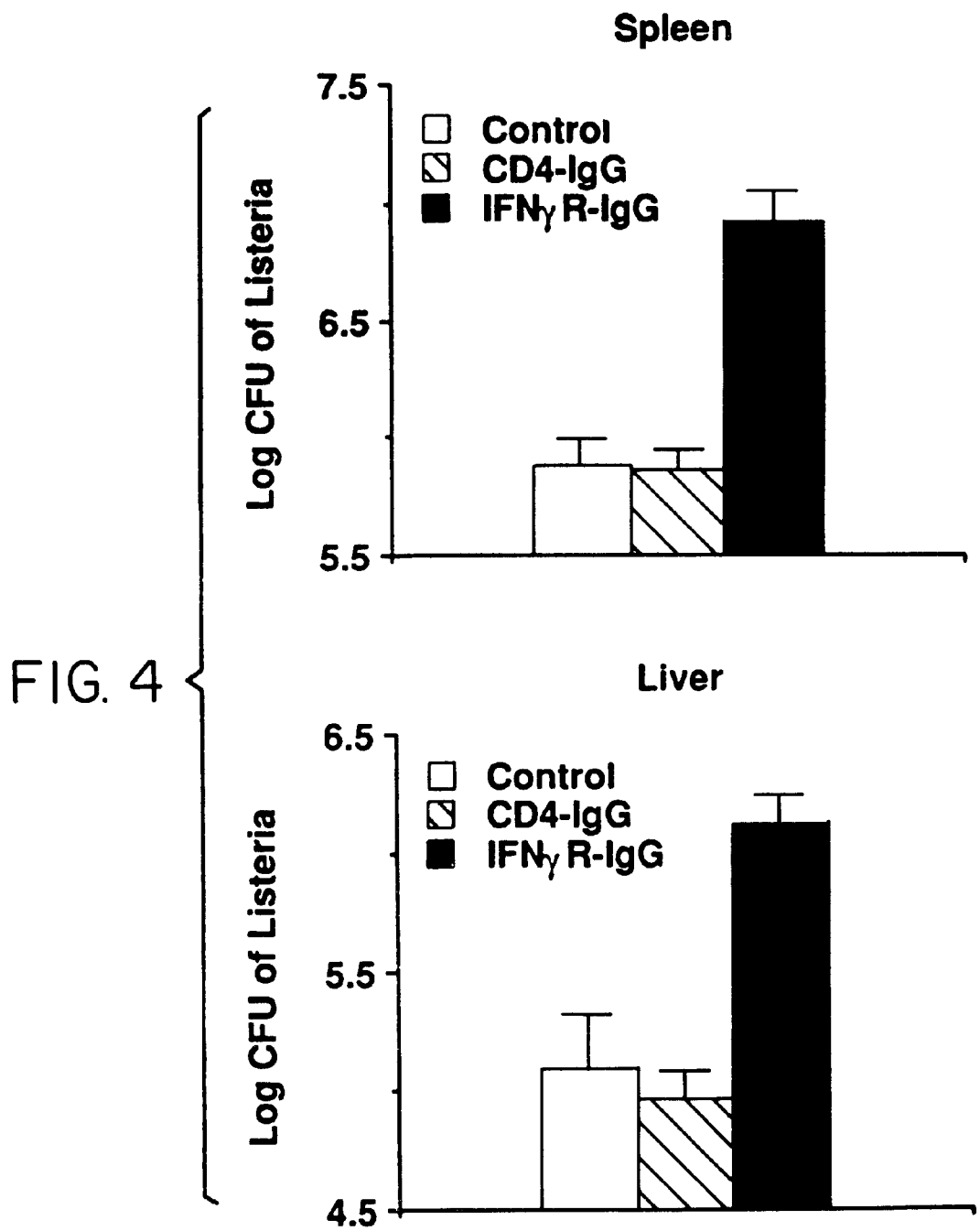
FIG. 4 is a set of graphs depicting inhibition of IFN-γ by IFNγR-IgG in a mouse model for Listeriosis. Mice were injected with vehicle (open bars), 200 µg of CD4-IgG (shaded bars), or 20 µg of mIFNGR-IgG (closed bars) followed immediately by 4×10$^4$ viable *Listeria monocytoaenes*. Three days later, spleen and liver homogenates were subcultured for 24 hours and colony-forming units (CFU) were enumerated. Data are means ±SEM (n=4 mice per group) from a representative experiment.

IFNγR-IgG blocks IFN-γ in vivo. To assess the ability of IFNγR-IgG to neutralize endogenous IFN-γ in vivo, we used a mouse model for the host immune response against infection with Listeria monocytogenes; in which IFN-γ is known to play a central role (Buchmier et al., supra; Farber et al., supra). Mice were given an i.p. injection of vehicle, CD4-IgG, or mIFNγR-IgG (200 µg), followed immediately with an LD, i.v. challenge of L. monocytogenes. Three days later, the number of bacterial colony forming units (CFU) in the spleens and livers of the mice were determined. Whereas CD4-IgG did not affect the number of CFU in either organ significantly, treatment with IFNγR-IgG resulted in about a ten-fold increase in the number of CFU in both spleen and liver (FIG. 4). Sequential analysis of bacterial loads over a period of 7 days following infection (data not shown) indicated that IFNγR-IgG affected the extent, and not the kinetics, of infection. These results indicate that the action of endogenous IFN-γ against infection with L. monocytogenes was inhibited effectively by IFNγR-IgG, thus demonstrating the ability of this immunoadhesin to block IFN-γ biological activity in vivo.

A relevant model for testing the ability of IFNγR-IgG to inhibit adverse consequences of inappropriate IFN-γ production in vivo is contact-sensitivity in mice. This immune response is based upon the interaction of an antigen with primed T-cells, and represents tissue damage resulting from inappropriate cell-mediated immunity, in which cytokines such as IFN-γ, TNF-α and IL-1 play an important role [Askenase, P. W. (1988) Effector and Regulatory Mechanisms in Delayed-Type Reed, E. F. Ellis and N. F. Atkinson, eds. C. V. Mosby, St. Louis; Enk and Katz, Proc. Natl. Acad. Sci. USA 89: 1398–1402 (1992); Belisto et al., J. Immunol. 143: 1530–1536 (1989); Piguet et al., J. Exp. Med. 173: 673.679 (1991)]. We sensitized mice to the hapten DNTP by topical administration to the abdomen. Five days later, the mice were challenged with DNFP by topical application to one pinna, whereas diluent was applied to the other pinna. Ten hours later, the mice received an i.v. injection of [$^{125}$I]UdR. Sixteen hours after isotope injection, the mice were euthanized and the pinnae were removed and analyzed for [$^{125}$I] incorporation, as a measure of lymphocyte proliferation and migration to the site of contact with antigen. Injection of mIFNγR-IgG (200 µg i.v. at priming and at challenge) resulted in about 44% inhibition of the response (Table 1).

TABLE 1

Inhibition of IFNγ by IFNγR-IgG in a mouse model for contact-sensitivity

| Treatment | Dose* (µg/mouse) | Response† (Fold) | Inhibition‡ (%) |
|---|---|---|---|
| Experiment 1 | | | |
| Vehicle | — | 1.21 ± 0.08 | — |
| IgG | 200 | 4.35 ± O.54 | 0 |
| IFNyR-IgG | 200 | 2.96 ± 0.46 | 44.3 |
| Experiment 2 | | | |
| Vehicle | — | 0.91 ± 0.15 | — |
| IgG | 50 | 4.42 ± 0.52 | 0 |
| IFNyR-IgG | 50 | 3.51 ± 0.37 | 25.9 |

TABLE 1-continued

Inhibition of IFNy by IFNyR-IgG in a mouse model for contact-sensitivity

| Treatment | Dose* (µg/mouse) | Response† (Fold) | Inhibition‡ (%) |
|---|---|---|---|
| TNFR-IgG | 50 | 3.54 ± 0.28 | 25.1 |
| IFNyR-IgG + TNFR-IgG | 50 + 50 | 2.80 ± 0.25 | 46.2 |
| Anti-mIFNy | 50 | 3.79 ± 0.49 | 17.9 |
| Anti-TNF | 50 | 3.77 ± 0.41 | 18.5 |
| Anti-IFNy + Anti-TNF | 50 + 50 | 2.37 ± 0.27 | 58.4 |

*Given i.v. at priming and at challenge.
†The numbers represent the ratio between [$^{125}$I] radioactivity measured in the antigen-painted pinna and the vehicle-painted pinna. Values are means ± SEM (n = 6 mice per treatment group).
‡Relative to the IgG control.

At a lower dose of 50 µg, less inhibition was observed (26%). It is likely that the inhibition of the response by IFNγR-IgG was not complete because other cytokines are involved in eliciting contact-sensitivity along with IFN-γ. Indeed, treatment with a TNF receptor immunoadhesin [TNFR1-IgG; Ashkenazi, A. et al., *Proc. Natl. Acad. Sci. USA* 88, 10535–10539 (1991)] at a dose of 50µg gave inhibition similar to IFNγR-IgG at 50 µg; moreover, a combination of the two immunoadhesins (50 µg each) resulted in an approximately additive inhibition of the response (Table 1). For comparison, we tested the effect of anti-IFN-γ and anti-TNF-α monoclonal antibodies. The extent of inhibition by these antibodies, when given individually or in combination was comparable to that observed with the IFNγR and TNFR immunoadhesins (Table 1). These results indicate that the contribution of IFN-γ to the contact-sensitivity response is inhibited effectively by IFNγR-IgG, thus demonstrating further the ability of this immunoadhesin to block IFN-γ biological activity in vivo.

In conclusion, each IFNγR-IgG immunoadhesin bound IFN-γ in a species-specific manner with nanomolar affinity, comparable to recombinant soluble IFN-γ receptors. In cultured cells, IFNγR-IgG was able to block completely IFN-γ-induced expression of ICAM 1 and MHC class I antigen, and IFN-γ antiviral activity. In mice, IFNγR-IgG inhibited the function of IFN-γ produced as a major cytokine in response to bacterial infection and in the elicitation of contact sensitivity. Thus, IFNγR-IgG is a specific and effective inhibitor of IFN-γ both in vitro and in vivo.

EXAMPLE 3

Inhibition of Gut Damage

The ability of IFN-γ receptor-IgG-1 chimeras to prevent gut damage characteristic of inflammatory bowel disease was tested in a model of fetal intestine explants. In this model, human fetal intestine explants are stimulated with staphylococcal exterotoxin B (SEB). This activates the lamina propria T cells expressing Vβ3 and the local cell-mediated immune response causes gut damage, which is seen as an increase in epithelial proliferation and the loss of matrix glycosaminoglycans due to the release of proteases and endoglycosydases by activated macrophages. This latter phenomenon is believed to be an important step in the production of ulcers in the gut.

Human small intestine was obtained within two hours of surgical termination from the Medical Research Council Foet al Tissue Bank. This study was conducted under conditions approved by the Hackney and District Health Authority ethical committee.

The small intestine (ileum) of a 15.3 week old fetus was dissected into 2-mm² explants and these were then cultured (20 per dish in 7 mls) with staphylococcal enterotoxin B (SEB) for 4 days at 37° C. in a 95% oxygen, 5% $CO_2$ atmosphere in 7 ml of serum-free CMRL-1066 medium (Flow Laboratories Inc., McLean, Va.), modified according to Autrup et al. [Rosenzweig and Kanwar, *Lab. Invest.* 47, 177–184 (1982)], but with the omission of hydrocortisone.

Separate cultures were set up with and anti-IL-2 antibodies (100 µl of cell culture supernatant, corresponding to only about 100–200 ng/ml of antibody), and a human IFN-γ receptor-IgG-1 chimera prepared as described in Example 1. These were added at the same time as SEB. At the end of the four days cultivation period, the tissues were snap frozen in liquid nitrogen, and stored at −70° C.

Frozen sections were cut to 6 µm sections, and the presence and distribution of lamina propria glycosaminoglycans (GAGs) visualized by silver staining [Klein et al., *Histochem. J.* 25, 291–298 (1993); Klein et al., *J. Cell. Sci.* 102,81–832 (1992)]. Specifically, anionic sites were visualized with a 5 nm gold-conjugated poly-L-lysine probe (Biocell Research Laboratories, Cardiff, U. K.) diluted 1 in 100 in phosphate-buffered saline, pH 1–2, free of calcium and magnesium. The probe was applied to the sections for 60 minutes, washed off with deionized water, and developed with a silver enhancer (Biocell) for about 15 minutes at room temperature. The slides were counterstained in Mayer's haemalum and mounted in Apathy's medium.

To quantify GAGs, multiple fields were scanned on an optical integrated densitometer. Units were chosen arbitrarily. The higher the number, the greater the staining and the greater the amount of GAGs in the tissue.

In the explants treated with SEB, the activated T cells secreted lymphokines which activated lamina propria acrophages. These then secrete met alloproteinases which degrade the extracellular matrix.

Figure 5:
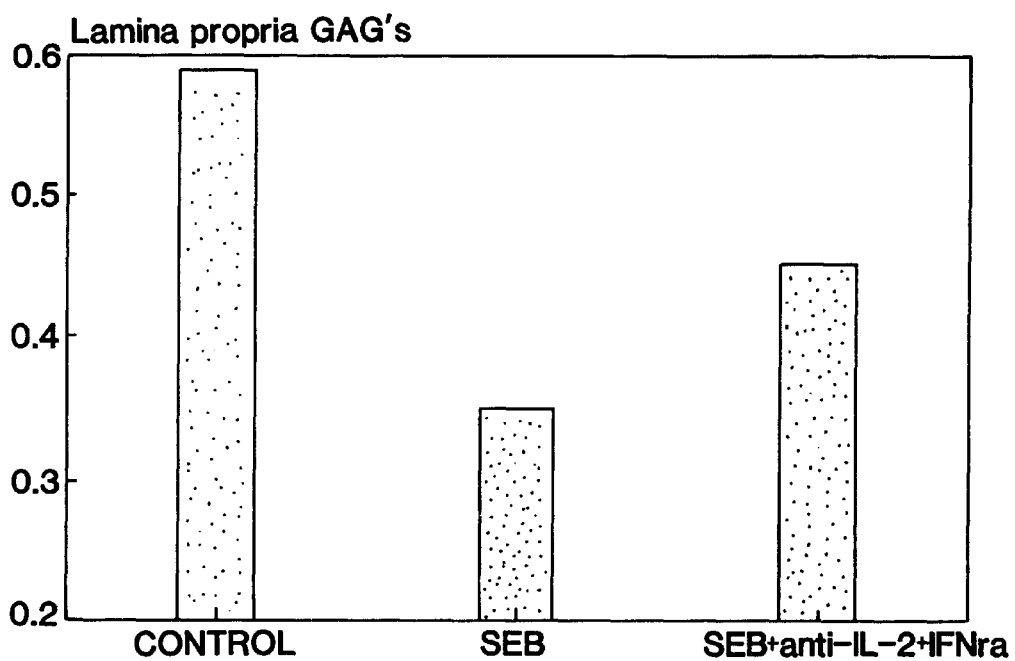
FIG. 5 is a graph that shows the amount of glycosaminoglycans (GAGs) in frozen sections of human fetal small intestines, as visualized by silver staining.

The data set forth in FIG. 5 show that the IFN-γ receptor-IgG-1 chimera was effective in preventing gut damage in this system. Although the test also included a minor amount of anti-IL-2 antibodies, the effect was clearly attributable to the IFN-γ-IgG-1 chimera, as in separate experiments, anti-IL-2 antibodies were found ineffective in this system.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

What is claimed is:

1. A method for treatment of inflammatory bowel disease patient, wherein the inflammatory bowel disease is ulcerative colitis comprising administering to the patient an effective amount of an interferon-gamma (IFN-γ) inhibitor, wherein the inhibitor inhibits the binding of native IFN-γ to its native receptor.

2. A method for treatment of inflammatory bowel disease in a patient, wherein the inflamatory bowel disease is Crohn's disease comprising admninistering to the patient an effective amount of an interferon-gamma (IFN-γ) inhibitor, wherein the inhibitor inhibits the binding of native IFN-γ to its native receptor.

3. The method according to claim 1, wherein said IFN-γ inhibitor comprises an anti-IFN-γ antibody, an IFN-γ receptor antibody or a native human IFN-γ receptor.

4. The method according to claim 3, wherein said IFN-γ inhibitor is an anti-IFN-γ antibody.

5. The method according to claim 3, wherein said IFN-γ inhibitor is an anti-IFN-γ receptor antibody.

6. The method according to claim 1, wherein said IFN-γ inhbitor comprises a native human IFN-γ receptor fragment capable of binding IFN-γ.

7. The method according to claim 5, wherein said IFN-γ receptor fragment is the extracellular portion of a native human IFN-γ receptor.

8. The method according to claim 7, wherein said IFN-γ receptor fragment is fused to a stable plasma protein.

9. The method according to claim 8, wherein said stable plasma protein is an immunoglobulin.

10. The method according to claim 2, wherein said IFN-γ inhibitor comprises an anti-IFN-γ antibody, an IFN-γ receptor antibody or a native human IFN-γ receptor.

11. The method according to claim 10, wherein said IFN-γ inhibitor is an anti-IFN-γ antibody.

12. The method according to claim 10, wherein said IFN-γ inhibitor is an anti-IFN-γ receptor antibody.

13. The method according to claim 2, wherein said IFN-γ inhibitor comprises a native human IFN-γ receptor fragment capable of binding IFN-γ.

14. The method according to claim 13, wherein said IFN-γ receptor fragment is the extracellular portion of a native human IFN-γ receptor.

15. The method according to claim 14, wherein said IFN-γ receptor fragment is fused to a stable plasma protein.

16. The method according to claim 15, wherein said stable plasma protein is an immunoglobulin.

17. A method according to claim 3, wherein the inhibitor is a native human IFN-γ receptor.

18. The method of claim 9, wherein said IFN-γ receptor fragment is fused to an immunoglobulin constant domain.

19. The method of claim 18, wherein the IFN-γ receptor fragment is fused, at its C-terminus, to the N-terminus of an immunoglobulin heavy chain constant domain.

20. The method of claim 19, wherein said immunoglobulin is composed of the hinge and Fc portion of an IgG heavy chain.

21. The method of claim 20, wherein said IgG is of the IgG-1 or IgG-3 isotype.

22. The method of claim 8, wherein said stable plasma protein is an albumin, a lipoprotein an apolipoprotein or tansferrin.

23. A method according to claim 10, wherein the inhibitor is a native human IFN-γ receptor.

24. The method of claim 16, wherein said IFN-γ receptor frment is fused to an immunoglobulin constant domain.

25. The method of claim 24, wherein the IFN-γ receptor fragment is fused, at its C-terminus, to the N-terminus of an immunoglobulin heavy chain constant domain.

26. The method of claim 25, wherein said immunoglobulin is composed of the hinge and Fc portion of an IgG heavy chain.

27. The method of claim 16, wherein said IgG is of the IgG-1 or IgG-3 isotype.

28. The method of claim 15, wherein said stable plasma protein is an albumin, a lipoprotein an apolipoprotein or transferrin.

* * * * *

UNITED STATES PATENT AND TRADEMARK OFFICE
CERTIFICATE OF CORRECTION

| | | |
|---|---|---|
| PATENT NO. | : 6,558,661 B1 | Page 1 of 4 |
| APPLICATION NO. | : 08/190204 | |
| DATED | : May 6, 2003 | |
| INVENTOR(S) | : Ashkenazi et al. | |

It is certified that error appears in the above-identified patent and that said Letters Patent is hereby corrected as shown below:

On Title Page Col. 1, (56) References Cited, insert the following:

U.S. PATENT DOCUMENTS

--5,551,658    9/1995            Seelig--

Under the heading "Other Publications" the following changes should be made:

Page 1, col. 1, under the reference Auguet et al. "Molecular Cloning …", "Auguet" should read --Agnet-- and "Inteferon" should read --Interferon--.

Page 2, col. 1, under the reference Dembic et al. "Prevention of streptozotocin …", "IFN-65 receptor immunoadhesions" should read --IFN-6γ receptor immunoadhesins--.

Page 2, col. 1, under the reference Ozmen et al. "Effect of soluble …", "development on spontaneous" should read --development of spontaneous--.

Page 2, col. 2, under the reference Brandtzaeg et al. "The Mucosal Immune System …" , "Immune System in inflammatory System in inflammatory Bowel Disease" should read --Immune System in inflammatory Bowel Disease--.

Col. 1, line 46:  "In,the" should read --In the--

Col. 3, line 38:  "eta/." should read --et. al.--

Col. 5, line 33:  "Locations of putative" should read --Locations of the putative--

Col. 5, line 37:  "transient by expression" should read --transient expression--

Col. 5, line 42:  "The proteins" should read --In FIG. 1B, the proteins--

Col. 5, line 44:  "introcellulose" should read --nitrocellulose--

Col. 5, line 50:  "chloronaphtot" should read --chloronapthol--

Col. 6, line 15:  "monocvtoaenes" should read --monocytogenes--

Col. 6, line 32:  "Inflamnatory" should read --Inflammatory--

UNITED STATES PATENT AND TRADEMARK OFFICE
CERTIFICATE OF CORRECTION

PATENT NO. : 6,558,661 B1
APPLICATION NO. : 08/190204
DATED : May 6, 2003
INVENTOR(S) : Ashkenazi et al.

It is certified that error appears in the above-identified patent and that said Letters Patent is hereby corrected as shown below:

Col. 6, line 35: "entities, Their" should read --entities, their--

Col. 6, line 41: "inmmunoglobulin" should read --immunoglobulin--

Col. 6, line 42: "The" should read --the--

Col. 6, line 48: "If The condition" should read --If the condition--

Col. 6, line 66: "A" should read --As--

Col. 10, line 19: "mino" should read --amino--

Col. 11, line 23: "Immunolooical" should read --Immunological--

Col. 13, line 11: "carbonyidiimidazole" should read --carbonyldiimidazole--

Col. 13, line 18: "Bioconiugate" should read --Bioconjugate--

Col. 14, line 3: "88109344" should read --88/09344--

Col. 16, line 37: "Laboratorv" should read --Laboratory--

Col. 17, line 10: "Exo." should read --Exp.--

Col. 17, line 27: "et a/." should read --et al.--

Col. 17, line 62: "rumors" should read --tumors--

Col. 17, line 64: "avaiable" should read --available--

Col. 20, line 35: "Saccharomves" should read --Saccharomyes--

Col. 22, line 16, "EXD." should read --Exp.--

Col. 25, line 29: "G1 ml" should read --Glml--

Col. 27, line 54: "non-$\alpha$ queous" should read --non-aqueous--

Col. 29, line 8: "Cia" should read --Cla--

UNITED STATES PATENT AND TRADEMARK OFFICE
CERTIFICATE OF CORRECTION

PATENT NO.        : 6,558,661 B1
APPLICATION NO. : 08/190204
DATED              : May 6, 2003
INVENTOR(S)       : Ashkenazi et al.

It is certified that error appears in the above-identified patent and that said Letters Patent is hereby corrected as shown below:

Col. 29, line 53: "IFNVR" should read --IFNγR--

Col. 30, line 14: "IFNv" should read --IFNγ--

Col. 31, line 12: "Balbic" should read --Balb/c--

Col. 31, line 23: "[12511" should read --[$^{125}$I]--

Col. 31, line 29: "IFNγR-IqG" should read --IFNγR-IgG--

Col. 31, line 35: "[1$^{125}$I]" should read --[$^{125}$I]--

Col. 31, line 49: "IFNγR-IaG" should read --IFNγR-IgG--

Col. 32, line 14: "LD" should read --LD$_{50}$--

Col. 41, claim 1, line 28: "disease patient" should read --disease in a patient--

Col. 41, claim 2, line 36: "admninistering" should read --administering--

Col. 41, claim 6, line 48: "inhbitor" should read --inhibitor--

Col. 41, claim 7, line 50: "claim 5" should read --claim 6--

Col. 42, claim 22, line 48: "a lipoprotein an" should read --a lipoprotein, an--

Col. 42, claim 24, line 53: "frment" should read --fragment--

UNITED STATES PATENT AND TRADEMARK OFFICE
CERTIFICATE OF CORRECTION

PATENT NO. : 6,558,661 B1
APPLICATION NO. : 08/190204
DATED : May 6, 2003
INVENTOR(S) : Ashkenazi et al.

It is certified that error appears in the above-identified patent and that said Letters Patent is hereby corrected as shown below:

Col. 42, claim 28, line 63: "a lipoprotein an" should read --a lipoprotein, an--

Signed and Sealed this

Fourteenth Day of November, 2006

JON W. DUDAS
*Director of the United States Patent and Trademark Office*

SEQUENCE LISTING

<160> NUMBER OF SEQ ID NOS: 2

<210> SEQ ID NO 1
<211> LENGTH: 2101
<212> TYPE: DNA
<213> ORGANISM: Homo sapiens
<220> FEATURE:
<221> NAME/KEY: CDS
<222> LOCATION: (49)..(1515)

<400> SEQUENCE: 1

```
gaattccgca ggcgctcggg gttggagcca gcgaccgtcg gtagcagc atg gct ctc         57
                                                    Met Ala Leu
                                                      1 ctc ttt ctc cta ccc ctt gtc atg cag ggt gtg agc agg gct gag atg         105
Leu Phe Leu Leu Pro Leu Val Met Gln Gly Val Ser Arg Ala Glu Met
        5                  10                  15 ggc acc gcg gat ctg ggg ccg tcc tca gtg cct aca cca act aat gtt         153
Gly Thr Ala Asp Leu Gly Pro Ser Ser Val Pro Thr Pro Thr Asn Val
 20                  25                  30                  35 aca att gaa tcc tat aac atg aac cct atc gta tat tgg gag tac cag         201
Thr Ile Glu Ser Tyr Asn Met Asn Pro Ile Val Tyr Trp Glu Tyr Gln
                 40                  45                  50 atc atg cca cag gtc cct gtt ttt acc gta gag gta aag aac tat ggt         249
Ile Met Pro Gln Val Pro Val Phe Thr Val Glu Val Lys Asn Tyr Gly
         55                  60                  65 gtt aag aat tca gaa tgg att gat gcc tgc atc aat att tct cat cat         297
Val Lys Asn Ser Glu Trp Ile Asp Ala Cys Ile Asn Ile Ser His His
     70                  75                  80 tat tgt aat att tct gat cat gtt ggt gat cca tca aat tct ctt tgg         345
Tyr Cys Asn Ile Ser Asp His Val Gly Asp Pro Ser Asn Ser Leu Trp
 85                  90                  95 gtc aga gtt aaa gcc agg gtt gga caa aaa gaa tct gcc tat gca aag         393
Val Arg Val Lys Ala Arg Val Gly Gln Lys Glu Ser Ala Tyr Ala Lys
100                 105                 110                 115 tca gaa gaa ttt gct gta tgc cga gat gga aaa att gga cca cct aaa         441
Ser Glu Glu Phe Ala Val Cys Arg Asp Gly Lys Ile Gly Pro Pro Lys
                120                 125                 130 ctg gat atc aga aag gag gag aag caa atc atg att gac ata ttt cac         489
Leu Asp Ile Arg Lys Glu Glu Lys Gln Ile Met Ile Asp Ile Phe His
            135                 140                 145 cct tca gtt ttt gta aat gga gac gag cag gaa gtc gat tat gat ccc         537
Pro Ser Val Phe Val Asn Gly Asp Glu Gln Glu Val Asp Tyr Asp Pro
        150                 155                 160 gaa act acc tgt tac att agg gtg tac aat gtg tat gtg aga atg aac         585
Glu Thr Thr Cys Tyr Ile Arg Val Tyr Asn Val Tyr Val Arg Met Asn
165                 170                 175 gga agt gag atc cag tat aaa ata ctc acg cag aag gaa gat gat tgt         633
Gly Ser Glu Ile Gln Tyr Lys Ile Leu Thr Gln Lys Glu Asp Asp Cys
180                 185                 190                 195 gac gag att cag tgc cag tta gcg att cca gta tcc tca ctg aat tct         681
Asp Glu Ile Gln Cys Gln Leu Ala Ile Pro Val Ser Ser Leu Asn Ser
                200                 205                 210 cag tac tgt gtt tca gca gaa gga gtc tta cat gtg tgg ggt gtt aca         729
Gln Tyr Cys Val Ser Ala Glu Gly Val Leu His Val Trp Gly Val Thr
            215                 220                 225 act gaa aag tca aaa gaa gtt tgt att acc att ttc aat agc agt ata         777
Thr Glu Lys Ser Lys Glu Val Cys Ile Thr Ile Phe Asn Ser Ser Ile
        230                 235                 240
```

-continued

```
aaa ggt tct ctt tgg att cca gtt gtt gct gct tta cta ctc ttt cta      825
Lys Gly Ser Leu Trp Ile Pro Val Val Ala Ala Leu Leu Leu Phe Leu
    245                 250                 255 gtg ctt agc ctg gta ttc atc tgt ttt tat att aag aaa att aat cca      873
Val Leu Ser Leu Val Phe Ile Cys Phe Tyr Ile Lys Lys Ile Asn Pro
260                 265                 270                 275 ttg aag gaa aaa agc ata ata tta ccc aag tcc ttg atc tct gtg gta      921
Leu Lys Glu Lys Ser Ile Ile Leu Pro Lys Ser Leu Ile Ser Val Val
                280                 285                 290 aga agt gct act tta gag aca aaa cct gaa tca aaa tat gta tca ctc      969
Arg Ser Ala Thr Leu Glu Thr Lys Pro Glu Ser Lys Tyr Val Ser Leu
            295                 300                 305 atc acg tca tac cag cca ttt tcc tta gaa aag gag gtg gtc tgt gaa     1017
Ile Thr Ser Tyr Gln Pro Phe Ser Leu Glu Lys Glu Val Val Cys Glu
        310                 315                 320 gag ccg ttg tct cca gca aca gtt cca ggc atg cat acc gaa gac aat     1065
Glu Pro Leu Ser Pro Ala Thr Val Pro Gly Met His Thr Glu Asp Asn
    325                 330                 335 cca gga aaa gtg gaa cat aca gaa gaa ctt tct agt ata aca gaa gtg     1113
Pro Gly Lys Val Glu His Thr Glu Glu Leu Ser Ser Ile Thr Glu Val
340                 345                 350                 355 gtg act act gaa gaa aat att cct gac gtg gtc ccg ggc agc cat ctg     1161
Val Thr Thr Glu Glu Asn Ile Pro Asp Val Val Pro Gly Ser His Leu
                360                 365                 370 act cca ata gag aga gag agt tct tca cct tta agt agt aac cag tct     1209
Thr Pro Ile Glu Arg Glu Ser Ser Ser Pro Leu Ser Ser Asn Gln Ser
            375                 380                 385 gaa cct ggc agc atc gct tta aac tcg tat cac tcc aga aat tgt tct     1257
Glu Pro Gly Ser Ile Ala Leu Asn Ser Tyr His Ser Arg Asn Cys Ser
        390                 395                 400 gag agt gat cac tcc aga aat ggt ttt gat act gat tcc agc tgt ctg     1305
Glu Ser Asp His Ser Arg Asn Gly Phe Asp Thr Asp Ser Ser Cys Leu
    405                 410                 415 gaa tca cat agc tcc tta tct gac tca gaa ttt ccc cca aat aat aaa     1353
Glu Ser His Ser Ser Leu Ser Asp Ser Glu Phe Pro Pro Asn Asn Lys
420                 425                 430                 435 ggt gaa ata aaa aca gaa gga caa gag ctc ata acc gta ata aaa gcc     1401
Gly Glu Ile Lys Thr Glu Gly Gln Glu Leu Ile Thr Val Ile Lys Ala
                440                 445                 450 ccc acc tcc ttt ggt tat gat aaa cca cat gtg cta gtg gat cta ctt     1449
Pro Thr Ser Phe Gly Tyr Asp Lys Pro His Val Leu Val Asp Leu Leu
            455                 460                 465 gtg gat gat agc ggt aaa gag tcc ttg att ggt tat aga cca aca gaa     1497
Val Asp Asp Ser Gly Lys Glu Ser Leu Ile Gly Tyr Arg Pro Thr Glu
        470                 475                 480 gat tcc aaa gaa ttt tca tgagatcagc taagttgcac caactttgaa            1545
Asp Ser Lys Glu Phe Ser
    485 gtctgatttt cctggacagt tttctgcttt aatttcatga aaagattatg atctcagaaa   1605 ttgtatctta gttggtatca accaaatgga gtgacttagt gtacatgaaa gcgtaaagag   1665 gatgtgtggc attttcactt ttggcttgta agtacagac ttttttttttt ttttaaacaa   1725 aaaaagcatt gtaacttatg aacctttaca tccagatagg ttaccagtaa cggaacatat   1785 ccagtactcc tggttcctag gtgagcaggt gatgccccag ggacctttgt agccacttca   1845 cttttttttct tttctctgcc ttggtatagc atatgtgttt tgtaagttta tgcatacagt   1905 aattttaagt aatttcagaa gaaattctcg aagcttttca aaattggact taaaatctaa   1965 ttcaaactaa tagaattaat ggaatatgta aatagaaacg tgtatatttt ttatgaaaca   2025
```

```
ttacagttag agatttttaa ataaagaatt ttaaaactca aaaaaaaaaa aaaaaaaaa    2085 aaaaaaaaag gaattc                                                   2101
```

<210> SEQ ID NO 2
<211> LENGTH: 489
<212> TYPE: PRT
<213> ORGANISM: Homo sapiens

<400> SEQUENCE: 2

```
Met Ala Leu Leu Phe Leu Leu Pro Leu Val Met Gln Gly Val Ser Arg
 1               5                  10                  15

Ala Glu Met Gly Thr Ala Asp Leu Gly Pro Ser Ser Val Pro Thr Pro
             20                  25                  30

Thr Asn Val Thr Ile Glu Ser Tyr Asn Met Asn Pro Ile Val Tyr Trp
         35                  40                  45

Glu Tyr Gln Ile Met Pro Gln Val Pro Val Phe Thr Val Glu Val Lys
     50                  55                  60

Asn Tyr Gly Val Lys Asn Ser Glu Trp Ile Asp Ala Cys Ile Asn Ile
 65                  70                  75                  80

Ser His His Tyr Cys Asn Ile Ser Asp His Val Gly Asp Pro Ser Asn
                 85                  90                  95

Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220

Gly Val Thr Thr Glu Lys Ser Lys Glu Val Cys Ile Thr Ile Phe Asn
225                 230                 235                 240

Ser Ser Ile Lys Gly Ser Leu Trp Ile Pro Val Val Ala Ala Leu Leu
                245                 250                 255

Leu Phe Leu Val Leu Ser Leu Val Phe Ile Cys Phe Tyr Ile Lys Lys
            260                 265                 270

Ile Asn Pro Leu Lys Glu Lys Ser Ile Ile Leu Pro Lys Ser Leu Ile
        275                 280                 285

Ser Val Val Arg Ser Ala Thr Leu Glu Thr Lys Pro Glu Ser Lys Tyr
    290                 295                 300

Val Ser Leu Ile Thr Ser Tyr Gln Pro Phe Ser Leu Glu Lys Glu Val
305                 310                 315                 320

Val Cys Glu Glu Pro Leu Ser Pro Ala Thr Val Pro Gly Met His Thr
                325                 330                 335

Glu Asp Asn Pro Gly Lys Val Glu His Thr Glu Leu Ser Ser Ile
            340                 345                 350
```

```
Thr Glu Val Val Thr Thr Glu Glu Asn Ile Pro Asp Val Val Pro Gly
        355                 360                 365

Ser His Leu Thr Pro Ile Glu Arg Glu Ser Ser Ser Pro Leu Ser Ser
        370                 375                 380

Asn Gln Ser Glu Pro Gly Ser Ile Ala Leu Asn Ser Tyr His Ser Arg
385                 390                 395                 400

Asn Cys Ser Glu Ser Asp His Ser Arg Asn Gly Phe Asp Thr Asp Ser
                405                 410                 415

Ser Cys Leu Glu Ser His Ser Ser Leu Ser Asp Ser Glu Phe Pro Pro
                420                 425                 430

Asn Asn Lys Gly Glu Ile Lys Thr Glu Gly Gln Glu Leu Ile Thr Val
            435                 440                 445

Ile Lys Ala Pro Thr Ser Phe Gly Tyr Asp Lys Pro His Val Leu Val
        450                 455                 460

Asp Leu Leu Val Asp Asp Ser Gly Lys Glu Ser Leu Ile Gly Tyr Arg
465                 470                 475                 480

Pro Thr Glu Asp Ser Lys Glu Phe Ser
                485
```